United States Patent
Klaubert et al.

(10) Patent No.: US 8,937,183 B2
(45) Date of Patent: Jan. 20, 2015

(54) DETECTION OF HYDROGEN PEROXIDE

(71) Applicant: Promega Corporation, Madison, WI (US)

(72) Inventors: Dieter Klaubert, Arroyo Grande, CA (US); John Shultz, Verona, WI (US); James Unch, Arroyo Grande, CA (US); Michael P. Valley, Fitchburg, WI (US); Hui Wang, San Luis Obispo, CA (US); Wenhui Zhou, San Luis Obispo, CA (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 14/336,877

(22) Filed: Jul. 21, 2014

(65) Prior Publication Data

US 2014/0329257 A1    Nov. 6, 2014

Related U.S. Application Data

(62) Division of application No. 13/587,387, filed on Aug. 16, 2012, now Pat. No. 8,785,652.

(60) Provisional application No. 61/524,066, filed on Aug. 16, 2011.

(51) Int. Cl.
| | | |
|---|---|---|
| C07F 5/04 | (2006.01) | |
| C07D 241/54 | (2006.01) | |
| C07D 235/00 | (2006.01) | |
| C12Q 1/66 | (2006.01) | |
| G01N 33/50 | (2006.01) | |

(52) U.S. Cl.
CPC ... C07F 5/04 (2013.01); C12Q 1/66 (2013.01); G01N 33/5038 (2013.01); C07D 241/54 (2013.01); C07D 235/00 (2013.01); G01N 2500/10 (2013.01)
USPC .............. 548/110; 544/229; 435/8

(58) Field of Classification Search
CPC ...... C07F 5/04; C07D 241/54; C07D 235/00; C12Q 1/66
USPC ............... 548/110; 544/229; 435/8
See application file for complete search history.

(56) References Cited

FOREIGN PATENT DOCUMENTS

| WO | 2011/133800 | 10/2011 |
| WO | 2013/025885 | 2/2013 |

OTHER PUBLICATIONS

Van de Bittner et al. In vivo imaging of hydrogen peroxide production in a murine tumor model with a chemoselective bioluminescent reporter:, PNAS, 2010, vol. 107, No. 50, pp. 21316-21321.*
Fieser and Fieser, "Fieser and Fieser's Reagents for Organic Synthesis," John Wiley and Sons (1994).
Gomi K et al: "Oxyluciferin, a luminescence product of firefly luciferase, is enzymatically regenerated into luciferin", Journal of Biological Chemistry, American Society for Biochemistry and Molecular Biology, US, vol. 276, No. 39, Sep. 28, 2001, pp. 36508-36513.
Greene and Wuts, "Protective Groups in Organic Synthesis," 2d. Ed., John Wiley and Sons (1991).
International Union of Pure and Applied Chemistry "Definitive Rules for Nomenclature of Organic Chemistry," J. Am. Chem. Soc. 1960, 82, 5566.
Invitrogen, "Amplex® Red Hydrogen Peroxide/Peroxidase Assay Kit", http://probes.invitrogen.com/media/pis/mp22188.pdf, 7 pages, (Jun. 26, 2009).
Larock, "Comprehensive Organic Transformations," VCH Publishers (1989).
Makena and Chung, "Evidence that 4-Aminobiphenyl, Benzidine, and Benzidine Congeners Produce Genotoxicity Through ReactiveOxygen Species," Environ. Mol. Mutagen. (2007), vol. 48, pp. 404-413.
Paquette, "Principles of Modem Heterocyclic Chemistry," Modern Heterocyclic Chemistry, (1968).
Paquette, ed., "Encyclopedia of Reagents for Organic Synthesis," John Wiley and Sons (1995).
Sun, JS et. al. "Menadione-induced cytotoxicity to rat osteoblasts," Cell Mol Life Sci (1997) vol. 53 pp. 967-976.
Tayor et al., "The Chemistry of Heterocyclic Compounds, A Series of Monographs" John Wiley & Sons, New York, 2000.
Van de Bittner et al. In vivo imaging of hydrogen peroxide production in a murine tumor model with a chemoselective bioluminescent reporter, PNAS, 2010, vol. 107, No. 50, pp. 21316-21321.
United States Patent Office Action for U.S. Appl. No. 13/587,387 dated Jul. 18, 2013 (6 pages).
PCT/US2012/051109 International Search Report and Written Opinion, dated Jan. 18, 2013 (16 pages).
PCT/US2012/051109 Invitation to Pay Additional Fees and International Search Report, dated Oct. 25, 2012 (6 pages).
United States Patent Office Notice of Allowance for U.S. Appl. No. 13/587,387 dated Mar. 17, 2014 (9 pages).

* cited by examiner

*Primary Examiner* — Joseph Kosack
(74) *Attorney, Agent, or Firm* — Michael Best & Friedrich LLP

(57) ABSTRACT

The present invention provides compounds useful for detection of hydrogen peroxide and methods of using same.

16 Claims, 4 Drawing Sheets

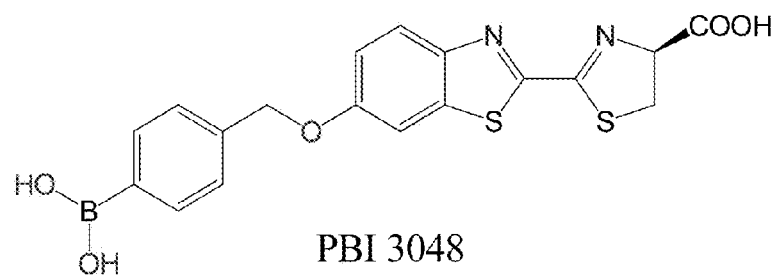
PBI 3048
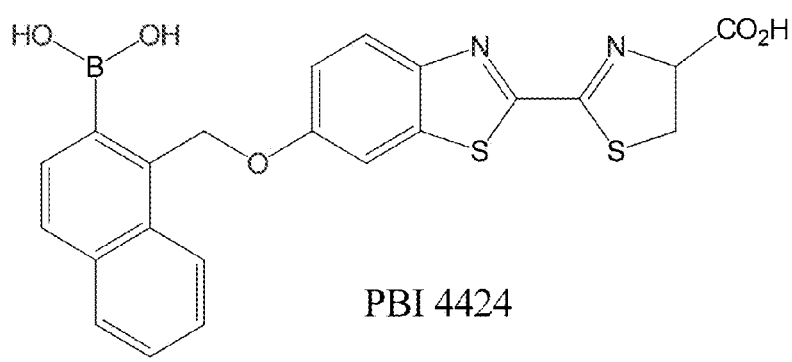
PBI 4424
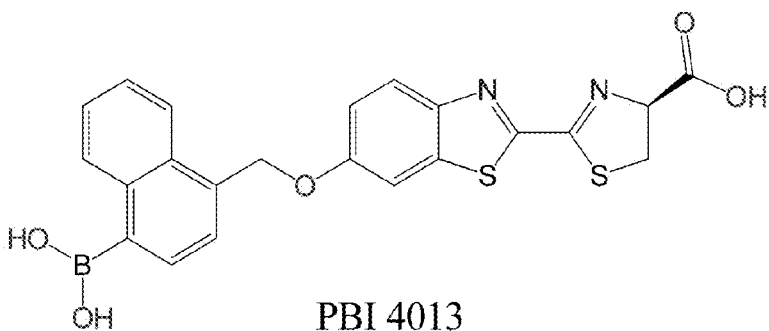
PBI 4013
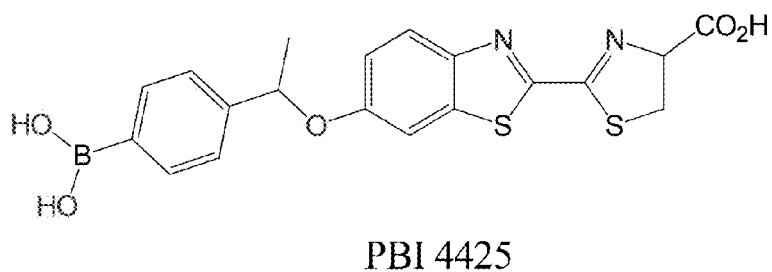
PBI 4425
FIG. 1

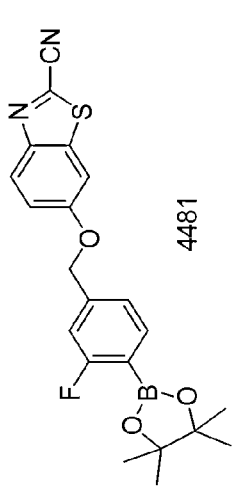
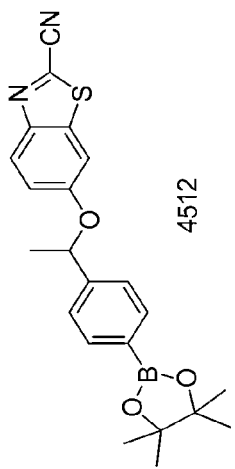
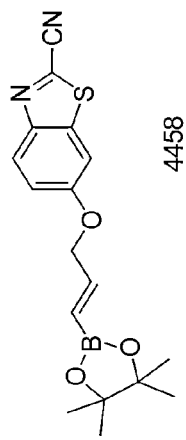
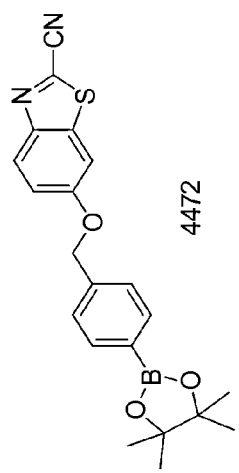
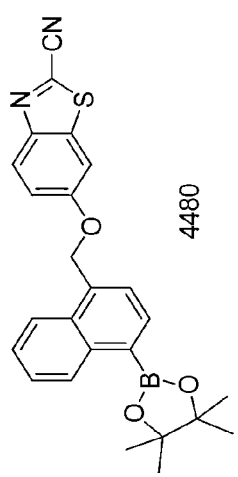
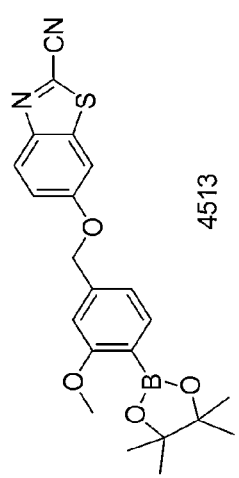
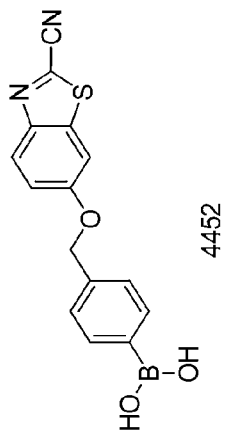
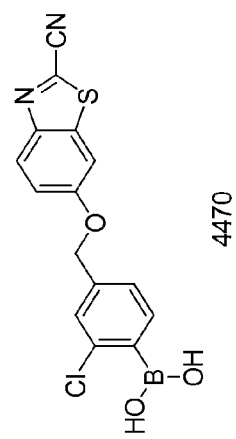
FIG. 2 pH 8.5

| | 0uM H2O2 | | | | 0.63uM H2O2 | | | | 1.25uM H2O2 | | | | 2.5uM H2O2 | | | |
|---|---|---|---|---|---|---|---|---|---|---|---|---|---|---|---|---|
| | No NL, No H2O2 | With NL, No H2O2 | With NL, With H2O2 | No NL, With H2O2 | No NL, No H2O2 | With NL, No H2O2 | With NL, With H2O2 | No NL, With H2O2 | No NL, No H2O2 | With NL, No H2O2 | With NL, With H2O2 | No NL, With H2O2 | No NL, No H2O2 | With NL, No H2O2 | With NL, With H2O2 | No NL, With H2O2 |
| Reading Set 1 | 20 | 106157 | 130346 | 30 | 29 | 95278 | 213650 | 38 | 30 | 81558 | 373664 | 42 | 32 | 82207 | 776020 | 37 |
| Reading Set 2 | 22 | 66920 | 83992 | 28 | 29 | 60292 | 376299 | 40 | 25 | 55158 | 628829 | 51 | 21 | 57119 | 1040926 | 50 |
| Reading Set 3 | 11 | 58006 | 73400 | 24 | 15 | 49426 | 357715 | 50 | 19 | 46165 | 548303 | 52 | 18 | 46834 | 788131 | 69 |
| Reading Set 4 | 10 | 50714 | 66247 | 20 | 12 | 41870 | 304518 | 47 | 20 | 38750 | 433562 | 69 | 22 | 39164 | 532356 | 60 |
| Reading Set 5 | 14 | 49202 | 64792 | 18 | 17 | 37859 | 250152 | 45 | 11 | 35858 | 320947 | 56 | 21 | 34929 | 326271 | 77 | pH 9.0

| | 0uM H2O2 | | | | 0.63uM H2O2 | | | | 1.25uM H2O2 | | | | 2.5uM H2O2 | | | |
|---|---|---|---|---|---|---|---|---|---|---|---|---|---|---|---|---|
| | No NL, No H2O2 | With NL, No H2O2 | With NL, With H2O2 | No NL, With H2O2 | No NL, No H2O2 | With NL, No H2O2 | With NL, With H2O2 | No NL, With H2O2 | No NL, No H2O2 | With NL, No H2O2 | With NL, With H2O2 | No NL, With H2O2 | No NL, No H2O2 | With NL, No H2O2 | With NL, With H2O2 | No NL, With H2O2 |
| Reading Set 1 | 21 | 84031 | 59810 | 20 | 24 | 98802 | 243734 | 28 | 28 | 81413 | 409040 | 42 | 13 | 72399 | 756209 | 40 |
| Reading Set 2 | 14 | 56994 | 41017 | 21 | 22 | 71773 | 320345 | 37 | 23 | 57915 | 505912 | 49 | 10 | 49490 | 785767 | 44 |
| Reading Set 3 | 25 | 46249 | 33442 | 20 | 17 | 59691 | 291229 | 38 | 18 | 48243 | 427623 | 52 | 17 | 39386 | 591410 | 65 |
| Reading Set 4 | 19 | 39798 | 28865 | 30 | 18 | 50554 | 238644 | 45 | 17 | 41806 | 326553 | 62 | 10 | 32441 | 398123 | 65 |
| Reading Set 5 | 21 | 36591 | 25800 | 19 | 16 | 47304 | 187211 | 37 | 18 | 38909 | 235174 | 54 | 17 | 28977 | 245647 | 75 |

FIG. 3

DETECTION OF HYDROGEN PEROXIDE

CROSS-REFERENCE TO RELATED APPLICATIONS

This application is a divisional of U.S. application Ser. No. 13/587,387, filed Aug. 16, 2012, now U.S. Pat. No. 8,785,652, which claims the benefit of U.S. Provisional Application No. 61/524,066, filed Aug. 16, 2011, which are incorporated by reference herein.

FIELD OF THE INVENTION

The present invention provides an assay for detection of hydrogen peroxide.

BACKGROUND OF THE INVENTION

To remain healthy, cells, in particular mammalian cells, need to maintain a balance between oxidizing and reducing conditions, sometime referred to as redox state/potential. Reactive oxygen species (ROS), including peroxides, are implicated in cellular activity and metabolism.

Effects of ROS on cell metabolism have been well documented in a variety of species. These include not only a role in apoptosis, but also in the induction of host defense genes and mobilization of ion transport systems. ROS are implicated in redox signaling, also known as oxidative signaling. In addition, ROS are implicated in cellular activity to a variety of inflammatory responses including cardiovascular disease. In general, harmful effects of ROS on a cell include: (a) damage of DNA; (b) oxidation of polyunsaturated fatty acids in lipids (lipid peroxidation); (c) oxidation of amino acids in proteins; and (d) inactivation of certain enzymes by oxidation of co-factors.

Hydrogen peroxide is generated in a variety of ways within the cell. Enzymes such as the monoamine oxidases produce hydrogen peroxide as a product of their enzymatic activity. Hydrogen peroxide can also be formed by interconversion of other reactive oxygen species such as that produced by superoxide dismutase when reacting with superoxide.

Current hydrogen peroxide detection techniques, such as AmplexRed, have several limitations including: requiring horseradish peroxidase, requiring an enzyme coupled assay, instability in the presence of thiols such as DTT, 2-mercaptoethanol, etc., and instablity at pH (>8.5).

SUMMARY

In one embodiment, the invention provides a compound according to Formula (I)

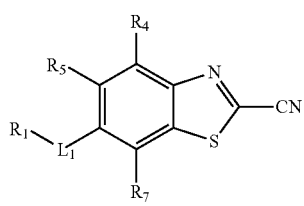

(I)

wherein
$R_1$ is boronic acid or a borate ester;
each $R_4$, $R_5$ and $R_7$ is independently selected from H, halo, methyl, and trifluoromethyl; and
$L_1$ is a linker.

The present invention also provides a compound according to Formula (II):

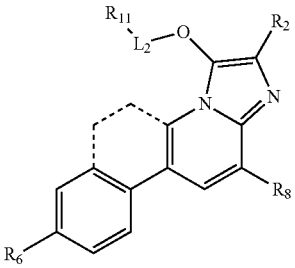

wherein
$R_{11}$ is boronic acid or a borate ester;
$R^2$ is —$(CH_2)_n$ or $C_{1-5}$ alkyl;
$R^6$ is selected from the group consisting of —H, —OH, —$NH_2$—OC(O)R or —$OCH_2OC(O)R$;
$R^8$ is selected from the group consisting of

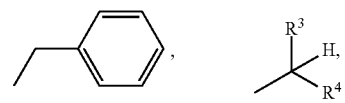

H or lower cycloalkyl;
wherein $R^3$ and $R^4$ are both H or both $C_{1-2}$ alkyl;
n is 0 to 3;
each R is independently a $C_{1-7}$ alkyl;
T is aryl, heteroaryl, substituted aryl, substituted heteroaryl or cycloalkyl;
$L_2$ is a linker;
and the dashed bonds indicate the presence of an optional ring which may be saturated or unsaturated.

In addition, the present invention provides a compound according to Formula (III):

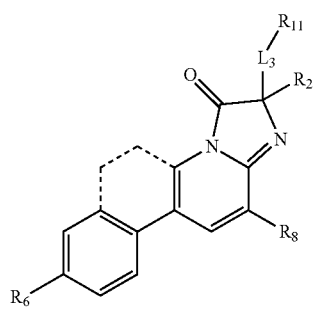

wherein
$R_{11}$ is boronic acid or a borate ester;
$R^2$ is —$(CH_2)_n$-T or $C_{1-5}$ alkyl;
$R^6$ is selected from the group consisting of —H, —OH, —$NH_2$—OC(O)R or —$OCH_2OC(O)R$;

$R^8$ is selected from the group consisting of

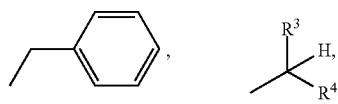

H or lower cycloalkyl;
wherein $R^3$ and $R^4$ are both H or both $C_{1-2}$ alkyl;
n is 0 to 3;
each R is independently a $C_{1-2}$ alkyl;
T is aryl, heteroaryl, substituted aryl, substituted heteroaryl or cycloalkyl;
$L_3$ is a linker;
and the dashed bonds indicate the presence of an optional ring which may be saturated or unsaturated.

In another embodiment, the invention provides a method of detecting hydrogen peroxide in a cell, wherein the cell is contacted with a compound according to Formula (I), (II) or (III) and a luciferase reaction mixture, and bioluminescence is measured thereby detecting the presence of hydrogen peroxide in the cell.

In yet another embodiment, the invention provides a method of detecting hydrogen peroxide in a cell, wherein the cell is contacted with a compound according to Formula (I), (II) or (III) to form an incubation mixture. At least a portion of the incubation mixture is transferred to a second reaction vessel, and a luciferase reaction mixture is added to the second reaction vessel. Bioluminescence is then measured thereby detecting the presence of hydrogen peroxide in the cell.

In a further embodiment, the invention provides a method of detecting hydrogen peroxide in a sample wherein a sample is contacted with a compound according to Formula (I), (II), or (III) and a luciferase reaction mixture and D-cysteine. Bioluminescence is then measured thereby detecting the presence of hydrogen peroxide in the sample.

In yet another embodiment, the invention provides a method of determining the effect of a test compound on the presence or amount of hydrogen peroxide in a sample wherein the sample is contacted with a test compound. A compound according to Formula (I), (II) or (III) and a luciferase reaction mixture is added, and bioluminescence is measured.

BRIEF DESCRIPTION OF THE FIGURES

FIG. 1. illustrates various luciferin borates.
FIG. 2. illustrates various benzothiazoles.
FIG. 3 shows sensitive detection of hydrogen peroxide using PBI 4759.

DETAILED DESCRIPTION OF THE INVENTION

Figure 4:
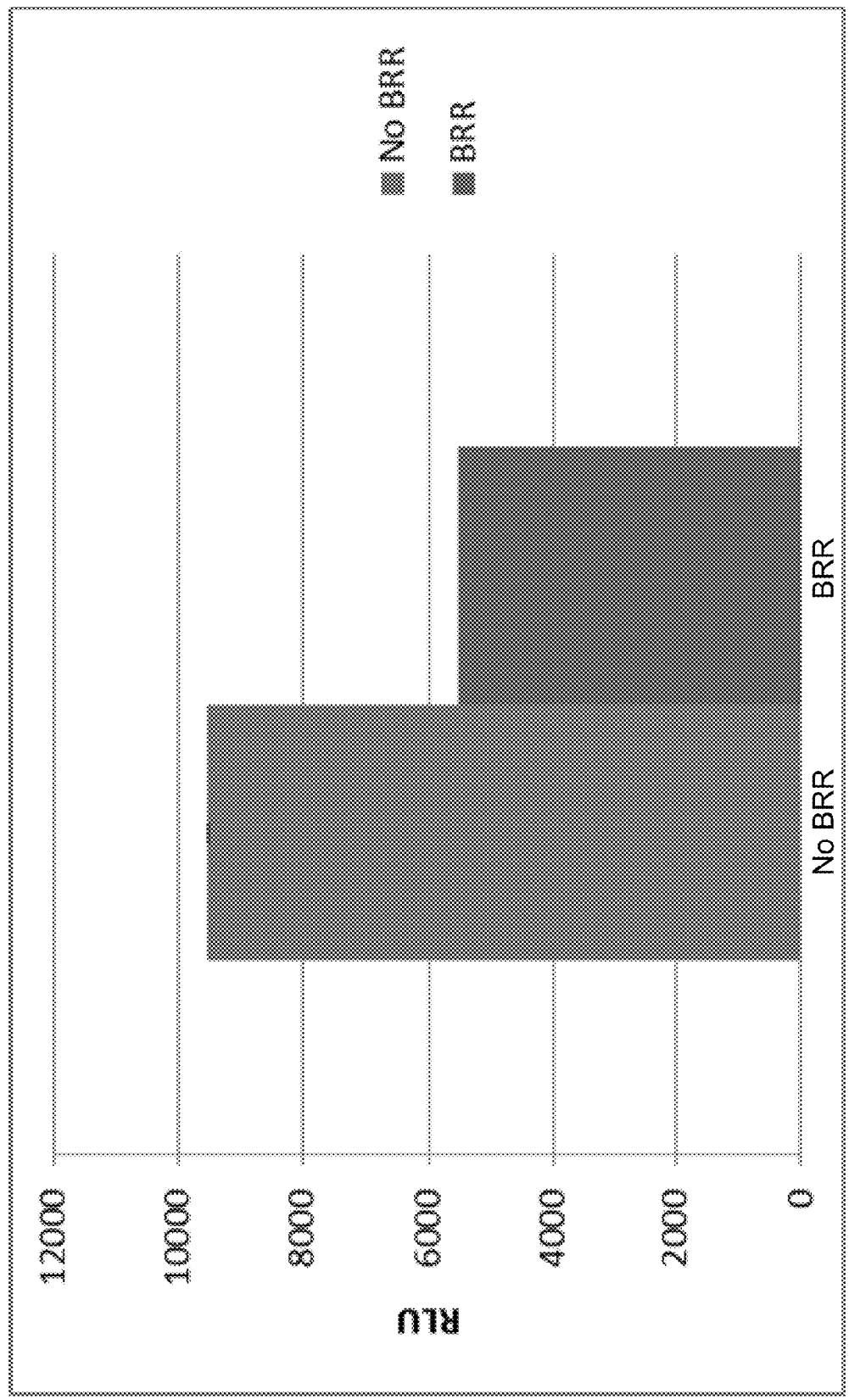
FIG. 4 shows addition of a reduction reagent can reduce background that may be seen with the luciferin borates such as PBI 4472.

The present invention provides compounds useful for detection of hydrogen peroxide and methods of using same.

DEFINITIONS

As used herein, the following terms and expressions have the indicated meanings. It will be appreciated that the compounds of the present invention contain asymmetrically substituted carbon atoms and may be isolated in optically active or racemic forms. It is well known in the art how to prepare optically active forms such as by resolution of racemic forms or by synthesis from optically active starting materials. All chiral, diastereomeric, racemic forms and all geometric isomeric forms of a structure are part of this invention.

Specific values listed below for radicals, substituents, and ranges, are for illustration only; they do not exclude other defined values or other values within defined ranges for the radicals and substituents.

As used herein, the term "substituted" is intended to indicate that one or more (e.g., 1, 2, 3, 4, or 5; in some embodiments 1, 2, or 3; and in other embodiments 1 or 2) hydrogens on the group indicated in the expression using "substituted" is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxylamine, hydroxyl(alkyl)amine, and cyano. Additionally, the suitable indicated groups can include, e.g., —X, —R, —O⁻, —OR, —SR, —S⁻, —NR₂, —NR₃, =NR, —CX₃, —CN, —OCN, —SCN, —N=C=O, —NCS, —NO, —NO₂, =N₂, —N₃, NC(=O) R, —C(=O)R, —C(=O)NRR, —S(=O)₂O⁻, —S(=O)₂ OH, —S(=O)₂R, —OS(=O)₂OR, —S(=O)₂NR, —S(=O)R, —OP(=O)O₂RR, —P(=O)O₂RR, —P(=O) (O)₂, —P(=O)(OH)₂, —C(=O)R, —C(=O)X, —C(S)R, —C(O)OR, —C(O)O, —C(S)OR, —C(O)SR, —C(S)SR, —C(O)NRR, —C(S)NRR, —C(NR)NRR, where each X is independently a halogen ("halo"): F, Cl, Br, or I; and each R is independently H, alkyl, aryl, heteroaryl, heterocycle, a protecting group or prodrug moiety. As would be readily understood by one skilled in the art, when a substituent is oxo (=O) or thioxo (=S), or the like, then two hydrogen atoms on the substituted atom are replaced.

As used herein, the term "alkyl" refers to a branched, unbranched, or cyclic hydrocarbon having, for example, from 1 to 30 carbon atoms, and often 1 to 12, or 1 to about 6 carbon atoms. Examples include, but are not limited to, methyl, ethyl, 1-propyl, 2-propyl, 1-butyl, 2-methyl-1-propyl, 2-butyl, 2-methyl-2-propyl(t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., alkylene).

The term "alkenyl" refers to a monoradical branched or unbranched partially unsaturated hydrocarbon chain (i.e. a carbon-carbon, sp² double bond). In one embodiment, an alkenyl group can have from 2 to 10 carbon atoms, or 2 to 6 carbon atoms. In another embodiment, the alkenyl group has from 2 to 4 carbon atoms. Examples include, but are not limited to, ethylene or vinyl, allyl, cyclopentenyl, 5-hexenyl, and the like. The alkenyl can be unsubstituted or substituted.

The term "alkynyl" refers to a monoradical branched or unbranched hydrocarbon chain, having a point of complete unsaturation (i.e. a carbon-carbon, sp triple bond). In one embodiment, the alkynyl group can have from 2 to 10 carbon atoms, or 2 to 6 carbon atoms. In another embodiment, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted.

The term "cycloalkyl" refers to cyclic alkyl groups of from 3 to 10 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can be unsubstituted or substituted. The cycloalkyl group can be monovalent or divalent, and can be optionally substituted as described above for alkyl groups. The cycloalkyl group can optionally include one or more cites of unsaturation, for example, the cycloalkyl group can include one or more carbon-carbon double bonds, such as, for example, cyclohexene, 1,3-cyclohexadiene, 1,4-cyclohexadiene, and the like.

The term "alkoxy" refers to the group alkyl-O—, where alkyl is as defined herein. In one embodiment, alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

As used herein, "aryl" or "Ar" refers to an aromatic hydrocarbon group derived from the removal of one hydrogen atom from a single carbon atom of a parent aromatic ring system. The radical can be at a saturated or unsaturated carbon atom of the parent ring system. The aryl group can have from 6 to 30 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups.

The term "halo" refers to fluoro, chloro, bromo, and iodo. Similarly, the term "halogen" refers to fluorine, chlorine, bromine, and iodine.

The term "haloalkyl" refers to alkyl as defined herein substituted by 1 or more halo groups as defined herein, which may be the same or different. In one embodiment, the haloalkyl can be substituted with 1, 2, 3, 4, or 5 halo groups. In another embodiment, the haloalkyl can by substituted with 1, 2, or 3 halo groups. The term haloalkyl also include perfluoro-alkyl groups. Representative haloalkyl groups include, by way of example, trifluoromethyl, 3-fluorododecyl, 12,12,12-trifluorododecyl, 2-bromooctyl, 3-bromo-6-chloroheptyl, 1H,1H-perfluorooctyl, and the like. The haloalkyl can be optionally substituted as described above for alkyl groups.

The term "heteroaryl" is defined herein as a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described above in the definition of "substituted". Typical heteroaryl groups contain 2-20 carbon atoms in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or ($C_1$-$C_6$)alkylaryl. In another embodiment heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, and sulfur, and optionally substituted with one or more groups as defined herein under the term "substituted". A heterocycle can be a monocyclic, bicyclic, or tricyclic group containing one or more heteroatoms. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The term "heterocycle" can include, by way of example and not limitation, a monoradical of the heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs"* (John Wiley & Sons, New York, 1950 to present), in particular Volumes 13, 14, 16, 19, and 28; and *J. Am. Chem. Soc.* 1960, 82, 5566. In one embodiment, "heterocycle" includes a "carbocycle" as defined herein, wherein one or more (e.g. 1, 2, 3, or 4) carbon atoms have been replaced with a heteroatom (e.g. O, N, or S).

Examples of heterocycles, by way of example and not limitation, include, dihydroypyridyl, tetrahydropyridyl(piperidyl), thiazolyl, tetrahydrothiophenyl, sulfur oxidized tetrahydrothiophenyl, pyrimidinyl, furanyl, thienyl, pyrrolyl, pyrazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In one embodiment, nitrogen bonded heterocycles include 1-aziridyl, 1-azetedyl, 1-pyrrolyl, 1-imidazolyl, 1-pyrazolyl, and 1-piperidinyl.

The term "carbocycle" refers to a saturated, unsaturated or aromatic ring having 3 to 8 carbon atoms as a monocycle, 7 to 12 carbon atoms as a bicycle, and up to about 30 carbon atoms as a polycycle. Monocyclic carbocycles typically have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo[5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. The carbocycle can be optionally substituted as described above for alkyl groups.

The term "alkanoyl" or "alkylcarbonyl" refers to —C(=O)R, wherein R is an alkyl group as previously defined.

The term "acyloxy" or "alkylcarboxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to —C(=O)OR (or "COOR"), wherein R is an alkyl group as previously defined.

The term "amino" refers to —NH$_2$. The amino group can be optionally substituted as defined herein for the term "substituted".

The term "alkylamino" refers to —NR$_2$, wherein at least one R is alkyl and the second R is alkyl or hydrogen.

The term "acylamino" refers to N(R)C(=O)R, wherein each R is independently hydrogen, alkyl, or aryl.

The term "hydroxyalkyl" refers to an alkyl group substituted by —OH.

The term "alkylcarboxylic acid" refers to an alkyl group substituted by —COOH.

The term "interrupted" indicates that another group is inserted between two adjacent carbon atoms (and the hydrogen atoms to which they are attached (e.g., methyl(CH$_3$), methylene (CH$_2$) or methine (CH))) of a particular carbon chain being referred to in the expression using the term "interrupted, provided that each of the indicated atoms' normal valency is not exceeded, and that the interruption results in a stable compound. Suitable groups that can interrupt a carbon chain include, e.g., with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) and sulfonyl(SO$_2$). Alkyl groups can be interrupted by one or more (e.g., 1, 2, 3, 4, 5, or about 6) of the aforementioned suitable groups. The site of interruption can also be between a carbon atom of an alkyl group and a carbon atom to which the alkyl group is attached.

The term "linker" refers to a (C$_1$-C$_{12}$)alkyl diradical that is optionally interrupted by one to four O atoms, N atoms, S atoms, or an optionally substituted aryl, heteroaryl, or heterocycle group.

The term "luciferase," unless specified otherwise, refers to a naturally occurring, recombinant or mutant luciferase. The luciferase, if naturally occurring, may be obtained easily by the skilled person from an organism. If the luciferase is one that occurs naturally or is a recombinant or mutant luciferase, i.e. one which retains activity in a luciferase-luciferin reaction of a naturally occurring luciferase, it can be obtained readily from a culture of bacteria, yeast, mammalian cells, insect cells, plant cells, or the like, transformed to express a nucleic acid encoding the luciferase. Further, the recombinant or mutant luciferase can be derived from an in vitro cell-free system using a nucleic acid encoding the luciferase. Luciferases are available from Promega Corporation, Madison, Wis.

As used herein, "bioluminescence" or "luminescence" is light produced as a result of a reaction between an enzyme and a substrate that generates light. Examples of such enzymes (bioluminescent enzymes) include firefly luciferase, e.g. *Photinus pyralis* or *Photinus pennslyvanica*, click beetle luciferase, cypridina luciferase, and the like.

A "luciferase reaction mixture" contains a luciferase enzyme and materials that will allow the luciferase enzyme to generate a light signal. The materials needed, and the particular concentrations and/or amounts, of the materials needed to generate a luminescent signal will vary depending on the luciferase enzyme used as well as the type of luciferase-based assay being performed. In general, for firefly luciferase, these materials can include: ATP, a magnesium (Mg$^{2+}$) salt, such as magnesium sulfate, a firefly luciferase enzyme, e.g, a thermostable firefly luciferase, and a luciferin capable of generating light when the luciferin is used as a substrate for the firefly luciferase. Often other materials will be added to the solution including: a buffer to maintain the reaction at the proper pH, an additive such as PRIONEX or Bovine serum albumin (BSA) to help maintain luciferase activity, reducing agents, detergents, esterases, salts, amino acids, e.g. D-cysteine, etc. An example luciferase reaction mixture would contain a thermostable firefly luciferase, MgSO$_4$, ATP, Tergitol NP-9, and Tricine. An alternative example luciferase reaction mixture would include Oplophorus luciferase, e.g., NanoLuc luciferase, buffer, e.g., Tris-Cl or Tris base, and optionally a background reduction agent, e.g., TCEP.

Compounds

In one aspect, the invention provides compounds according to Formula (I):

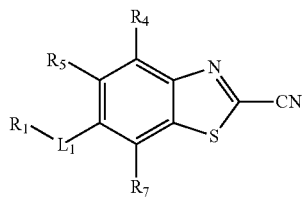
(I)

wherein

R₁ is boronic acid or a borate ester;

each R₄, R₅ and R₇ is independently selected from H, halo, methyl, and trifluoromethyl;

and

L₁ is a linker.

In certain embodiments, R₁ is a borate ester. For example, R₁ can be —B(OR₆)₂; wherein each R₆ is independently selected from H and $C_{1-4}$ alkyl.

R₁ may also be

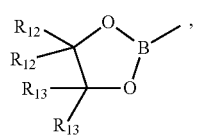

wherein each R₁₂ and R₁₃ is independently selected from H, $C_{1-4}$ alkyl, CF₃, phenyl or substituted phenyl. Alternatively, R₁₂ and R₁₃ together can be an alkyl ring having from 3-7 carbons or can be replaced by a fused 6-membered aromatic ring.

In addition, R₁ may be

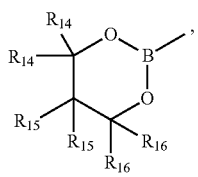

wherein each R₁₄, R₁₅ and R₁₆ is independently selected from H, $C_{1-4}$ alkyl, CF₃, phenyl and substituted phenyl. Alternatively, both R₁₅ together can form an alkyl ring having from 3-7 carbons; R₁₄ and R₁₅ together or R₁₅ and R₁₆ together can be an alkyl ring having from 3-7 carbon atoms or can be replaced by a 6-membered aromatic ring.

In certain embodiments, L₁ is

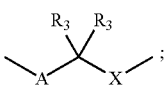

A is —C₆(R₁₀)₄— or —(CR₁₁=CR₁₁)ₙ— or a direct bond or —O—(C₆(R₁₀)₄— or —S—C₆(R₁₀)₄— or —NR'—C₆(R₁₀)₄; R' is H or $C_{1-4}$ alkyl; each R₃ is independently halo, H, $C_{1-4}$ alkyl, $C_{1-4}$ hydroxyalkyl, or $C_{1-4}$ alkylcarboxylic acid; each R₁₀ is independently H, halo, CH₃, OCH₃, or NO₂; each R₁₁ is independently H or CH₃; n is 1 or 2; and X is selected from —O—,

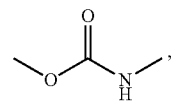

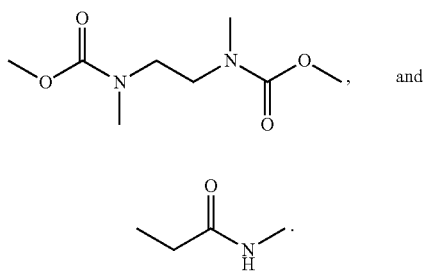
and

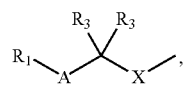

In some embodiments, -L₁-R₁ is

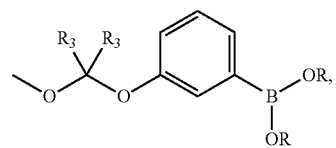

In additional embodiments, -L₁-R₁ is

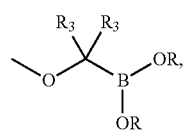

where A is —O—(C₆H₄)— and X is —O—. In other embodiments, -L₁-R₁ is

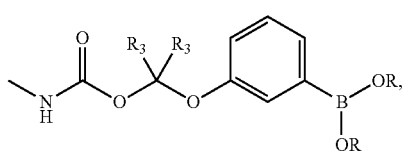

where A is a direct bond and X is —O—.

In certain embodiments, -L₁-R₁ is

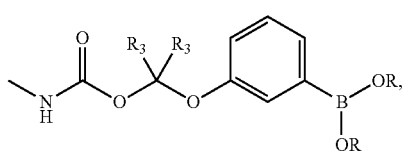

where A is —O—(C₆H₄)— and X is —NHCO₂—. In certain embodiments, -L₁-R₁ is

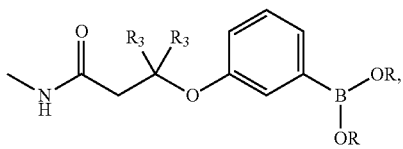

where A is —O—(C$_6$H$_4$)— and X is —NHC(O)CH$_2$—.

Suitable compounds according to Formula (I) include those shown in FIG. 2 and below:

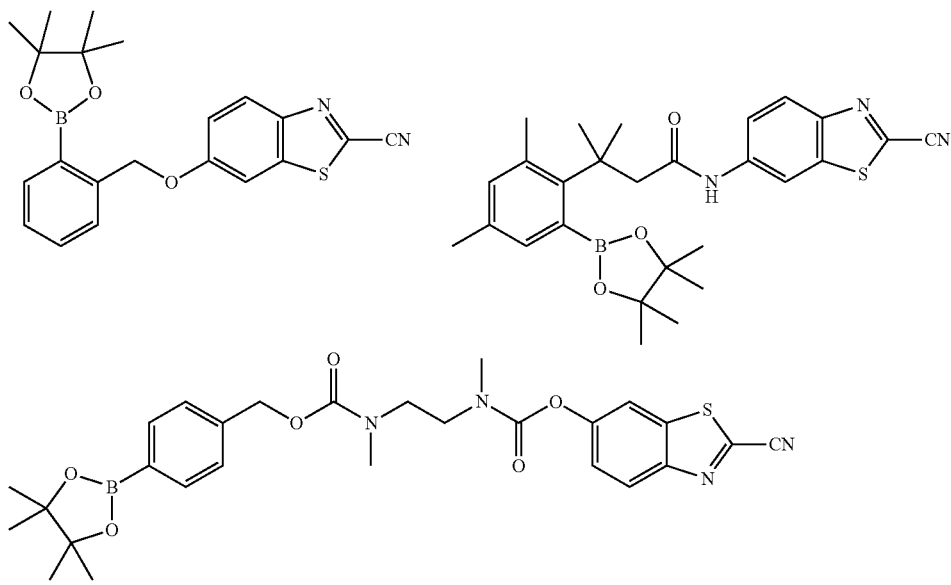

In another embodiment, the present invention provides a compound of Formula (II):

[Formula II structure]

or Formula (III):

[Formula III structure]

wherein

R$_{11}$ is boronic acid or a borate ester;

R$^2$ is —(CH$_2$)$_n$-T or C$_{1-5}$ alkyl;

R$^6$ is selected from the group consisting of —H, —OH, —NH$_2$—OC(O)R or —OCH$_2$OC(O)R;

R$^8$ is selected from the group consisting of

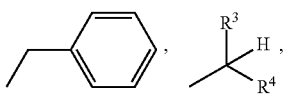

H or lower cycloalkyl;

wherein R$^3$ and R$^4$ are both H or both C$_{1-2}$ alkyl;

n is 0 to 3;

each R is independently a C$_{1-7}$ alkyl;

T is aryl, heteroaryl, substituted aryl, substituted heteroaryl or cycloalkyl;

L$_2$ or L$_3$ is a linker;

and the dashed bonds indicate the presence of an optional ring which may be saturated or unsaturated.

In certain embodiments, R$_{11}$ is a borate ester. For example, R$_{11}$ can be —B(OR$_7$)$_2$; wherein each R$_7$ is independently selected from H and C$_{1-4}$ alkyl.

R$_{11}$ may also be

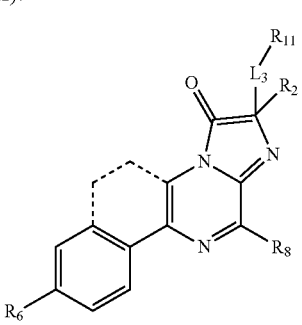

wherein each R$_{12}$ and R$_{13}$ is independently selected from H, C$_{1-4}$ alkyl, CF$_3$, phenyl or substituted phenyl. Alternatively, R$_{12}$ and R$_{13}$ together can be an alkyl ring having from 3-7 carbons or can be replaced by a fused 6-membered aromatic ring.

In addition, $R_{11}$ may be

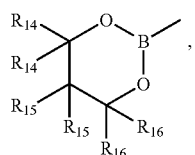

wherein each $R_{14}$, $R_{15}$ and $R_{16}$ is independently selected from H, $C_{1-4}$ alkyl, $CF_3$, phenyl and substituted phenyl. Alternatively, both $R_{15}$ together can form an alkyl ring having from 3-7 carbons; $R_{14}$ and $R_{15}$ together or $R_{15}$ and $R_{16}$ together can be an alkyl ring having from 3-7 carbon atoms or can be replaced by a 6-membered aromatic ring.

In certain embodiments, $L_2$ is

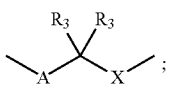

A is —$C_6(R_{10})_4$— or —$(CR_{21}=CR_{21})_n$— or —O—$C_6(R_{10})_4$— or —S—$C_6(R_{10})_4$— or —NR'—$C_6(R_{10})_4$— or a direct bond; R' is H or $C_{1-4}$ alkyl; each $R_3$ is independently halo, H, $C_{1-4}$ alkyl, $C_{1-4}$ hydroxyalkyl, or $C_{1-4}$ alkylcarboxylic acid; each $R_{10}$ is independently H, halo, $CH_3$, $OCH_3$, or $NO_2$; each $R_{21}$ is independently H or $CH_3$; n is 1 or 2; and X is selected from a direct bond, —C(O)—, and —C(O)$NR_{22}$, where $R_{22}$ is H or $C_{1-4}$ alkyl.

In some embodiments, -$L_2$-$R_{11}$ is

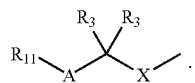

In certain embodiments, $L_3$ is

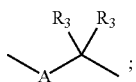

wherein A is —$C_6(R_{10})_4$—, or —$(CR_{21}=CR_{21})_n$—; each $R_3$ is independently halo, H, $C_{1-4}$ alkyl, $C_{1-4}$ hydroxyalkyl, or $C_{1-4}$ alkylcarboxylic acid; each $R_{10}$ is independently H, halo, $CH_3$, $OCH_3$, or $NO_2$; each $R_{21}$ is independently H or $CH_3$; and n is 1 or 2.

In certain embodiments, -$L_3$-$R_{11}$ is

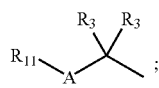

In some embodiments, $R^2$ is

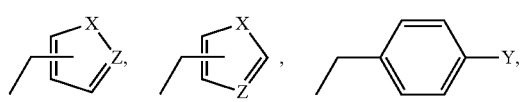

or $C_{2-5}$ alkyl; each X is independently —S—, —O— or —NH—; Z is —CH— or —N—; Y is —H or —OH; W is —$NH_2$, halo, —OH, —NHC(O)R, —$CO_2$R; and R is $C_{1-7}$ alkyl.

In some embodiments, $R^2$ is

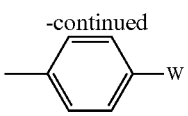

and X is O or S. In other embodiments, $R^2$ is $C_{2-5}$ straight-chain alkyl. In certain embodiments, $R^8$ is

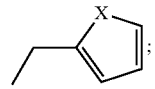

lower cycloalkyl or H, wherein $R^3$ and $R^4$ are both H or $C_{1-2}$ alkyl. In other embodiments, $R^8$ is benzyl.

Suitable compounds according to Formula (II) include:

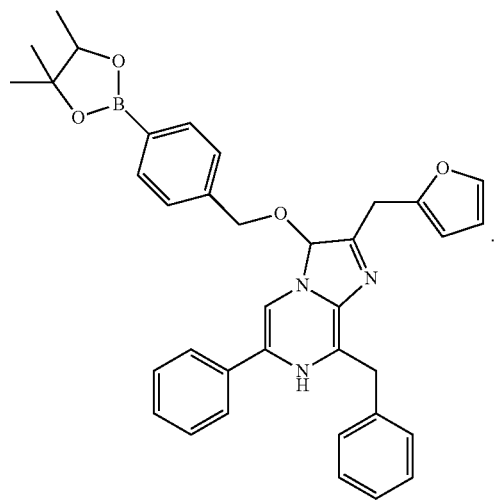 [SMILES: CC1OB(c2ccc(COC3C(Cc4ccco4)=NC4=C(Cc5ccccc5)NC(c5ccccc5)=CN43)cc2)OC1(C)C]

Synthesis of Compounds

Compounds described herein may be synthesized using a variety of methods. Exemplary syntheses are generalized in Schemes 1 and 2 below.

Scheme 1

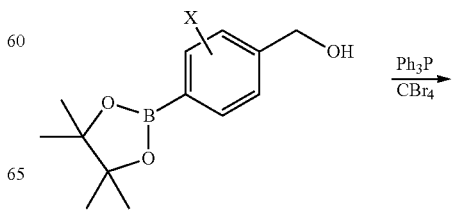

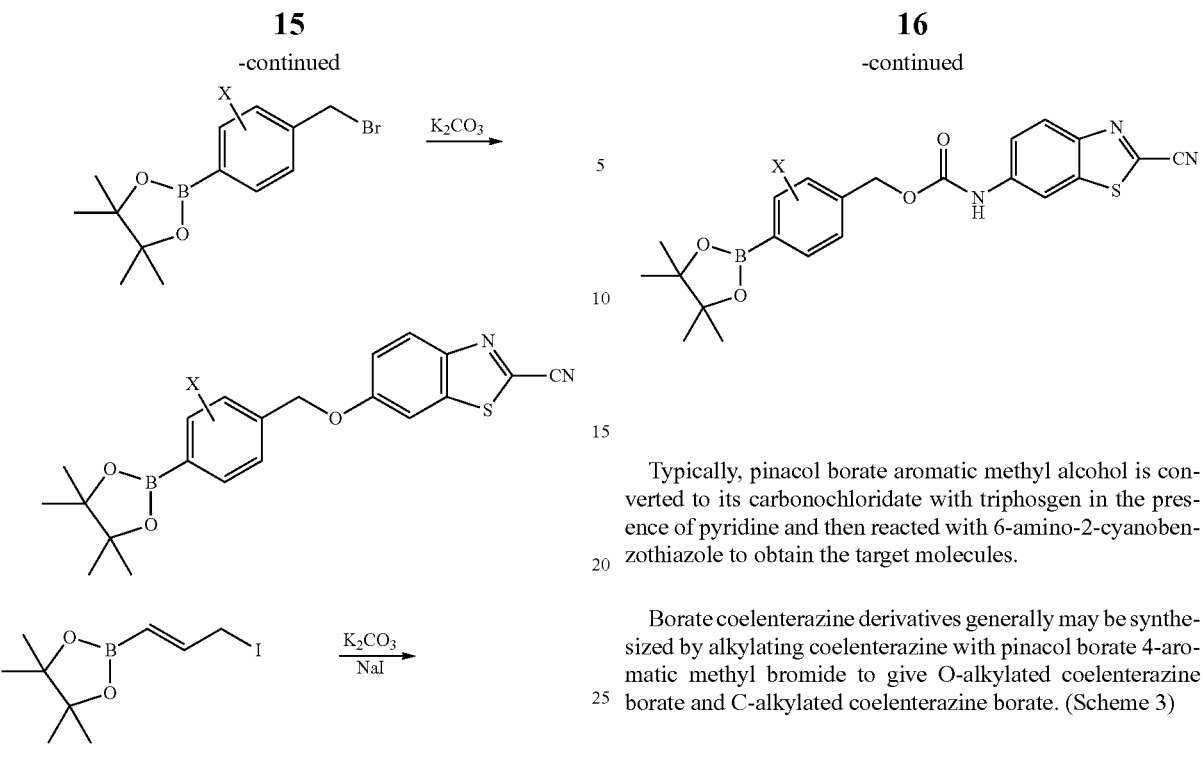

The synthesis of a pinacol borate of aromatic benzyl-6-O-2-cyanobenzothiazole can be accomplished by two steps. Typically, borate pinacol ester 4-aromatic methyl alcohol is converted into pinacol borate 4-aromatic methyl bromide with Ph₃P and CBr₄, and then reacted with 2-cyano-6-hydroxybenzothiazole in the presence of $K_2CO_3$ to obtain the desired compound. The synthesis of pinacol borate of ally-6-O-2-cyanobenzothiazole can be completed by direct alkylation of 6-hydroxy-2-cyanobenzothiazole with pinacol borate ally iodide. (Scheme 1)

Typically, pinacol borate aromatic methyl alcohol is converted to its carbonochloridate with triphosgen in the presence of pyridine and then reacted with 6-amino-2-cyanobenzothiazole to obtain the target molecules.

Borate coelenterazine derivatives generally may be synthesized by alkylating coelenterazine with pinacol borate 4-aromatic methyl bromide to give O-alkylated coelenterazine borate and C-alkylated coelenterazine borate. (Scheme 3)

Scheme 3

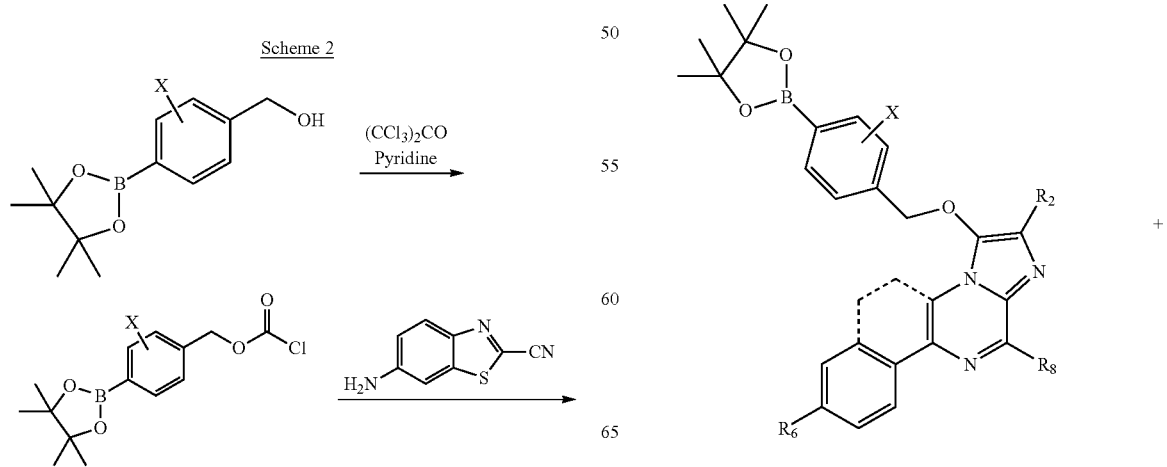

-continued

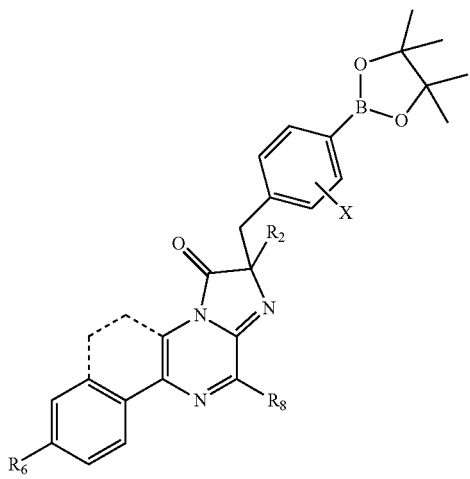

As can be appreciated by the skilled artisan, alternative methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Methods of Use

In an aspect, the invention provides a method of detecting hydrogen peroxide. In one embodiment, a sample is contacted with a compound according to Formula (I), (II) or (III) described herein to form a first mixture. At least a portion of the first mixture is contacted with a luciferase reaction mixture and D-cysteine. Bioluminescence is detected thereby detecting the presence of hydrogen peroxide.

In another embodiment of the present invention, cells are contacted with a compound according to Formula (I), (II) or (III) described herein, a luciferase reaction mixture is added to the contacted cells, and bioluminescence is detected. In certain embodiments, D-luciferin is also added to the contacted cells.

In another aspect, the invention provides a method for determining the effect of a test compound or test condition on the presence or amount of hydrogen peroxide in a sample, cell or animal. In one embodiment, the sample, cells or animal are contacted with a test compound or test condition prior to being contacted with a compound according to Formula (I), (II) or (III) described herein and a luciferase reaction mixture. The effect of the test compound or test condition on the presence or amount of hydrogen peroxide in the sample or cells is determined by detecting bioluminescence. Suitably, the test condition may be a change in temperature, oxygen tension, or ionic strength or an osmotic change.

The reagents may be added sequentially or simultaneously. If the reagents are added simultaneously, they may be in a single solution or multiple solutions.

The signal may be quantified if desired. The signal may be compared to a standard curve. The intensity of the signal is a function of the presence of amount of hydrogen peroxide in the sample. The signal may also be compared to a control.

The present invention may be used to determine the presence or amount of hydrogen peroxide in cells grown in culture medium or in cells within animals, e.g., living animals. For research purposes, for measurements in cells in animals, a compound according to Formula (I), (II) or (III) described herein is administered, e.g., injected into the animal or added to an aqueous solution, e.g., water, or food consumed by the animal, to the animal. Conversion of the compound to a product that is a luciferase substrate may be detected by bioluminescence mediated by luciferase expressed in cells in the animal, e.g., whole animal imaging of a transgenic animal (e.g., mice, rats, and marmoset monkeys) by luciferase administered to the animal, e.g., injected into the animal, or by collecting physiological fluids, e.g., blood, plasma, urine, and the like, or tissue samples, and combining those with a luciferase reaction mixture.

Cells may be eukaryotic cells, e.g., yeast, avian, plant, insect or mammalian cells, including but not limited to human, simian, murine, canine, bovine, equine, feline, ovine, caprine or swine cells, or prokaryotic cells, or cells from two or more different organisms, or cell lysates or supernatants thereof. The cells may have been genetically modified via recombinant techniques. In certain aspects, the cell may be in an animal, e.g., transgenic animals, or physiological fluid, e.g., blood, plasma, urine, mucous secretions or the like. Destruction of the cells is not required as the media can be sampled.

In addition, for any of the bioluminogenic assays described herein, other reagents may be added to reaction mixtures, including but not limited to those that inhibit or prevent inactivation of luciferase, or otherwise extend or enhance the bioluminescent signal.

The bioluminescence generated may be compared to a control. Suitable controls lack one or more of the necessary components or conditions for either the reaction between the compound and hydrogen peroxide or the luciferase reaction. Such components or conditions include, but are not limited to, co-factors, enzyme, temperature, and inhibitors.

Suitable substrates include, but are not limited to, compounds of Formulas (I) or (II) described herein.

Certain substrates may be particularly advantageous for use in various embodiments of this invention. For example, certain substrates may be better suited to use in vitro and others may be better suited to use in vivo. As would be recognized by one of ordinary skill in the art, not all borates would be suitable for use in the methods of the present invention. For example, small changes in the compounds can affect the reactivity toward hydrogen peroxide or the ability to work in certain assay conditions.

The invention is further described by the following non-limiting examples.

EXAMPLES

Example 1

6-((4-(4,4,5,5-tetramethyl-1,3,2-dioxaborolan-2-yl)benzyl)oxy)benzo-[d]thiazole-2-carbonitrile (PBI 4472)

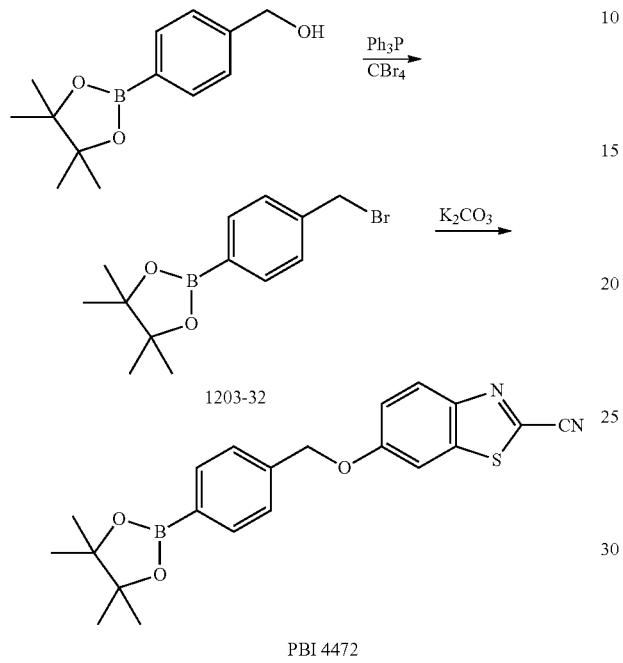

PBI 4472

Synthesis of 2-(4-(bromomethyl)phenyl)-4,4,5,5-tetramethyl-1,3,2-dioxaborolane (1203-32)

4-hydroxymethylphenylboronic acid, pinacol ester (1.08 g, 4.61 mmol) was dissolved in THF (20 ml) together with triphenylphosphine (2.42 g, 9.23 mmol). The reaction mixture was cooled in an ice-water bath, and carbon tetrabromide (3.06 g, 9.23 mmol) was added portionwise. After stirring for 4 hours at room temperature, the reaction mixture was poured into water and extracted with ethyl acetate. The organic layer was combined and dried by sodium sulfate. After filtration, the solvent was evaporated, and the residue was purified by flash chromatography to give the product as a white solid (1.72 g, 92%). $^1$H NMR (300 MHz, CD$_2$Cl$_2$, δ): 7.62 (d, J=6.0 Hz, 2H), 7.32 (d, J=6.0 Hz, 2H), 4.58 (d, 2H), 1.34 (s, 9H); MS (ESI) m/z 297.0.

Synthesis of 6-((4-(4,4,5,5-tetramethyl-1,3,2-dioxaborolan-2-yl)benzyl)oxy)benzo-[d]thiazole-2-carbonitrile (PBI 4472)

A mixture of 6-hydroxybenzothiazole (0.5 g, 2.84 mmol), potassium carbonate (0.78 g, 5.68 mmol) and potassium iodide (0.94 g, 5.68 mmol) in acetonitrile was heated to reflux for 1 hour. 2-(4-(bromomethyl)phenyl)-4,4,5,5-tetramethyl-1,3,2-dioxaborolane (0.93 g, 3.12 mmol) was added, and the reaction mixture was refluxed overnight. After cooling down, the suspension was extracted with ethyl acetate/water and the residue was purified with flash chromatography to give the product as a white solid (0.8 g, 72%). $^1$H NMR (300 MHz, CD$_2$Cl$_2$, δ): 8.11 (d, J=9.0 Hz, 1H), 7.81 (d, J=9.0 Hz, 2H), 7.47 (m, 3H), 7.34 (dd, J=9.0 Hz, 1H), 5.22 (s, 2H), 1.35 (s, 9H); MS (ESI) m/z 393.2.

Example 2

(4-(((2-cyanobenzo[d]thiazol-6-yl)oxy)methyl)phenyl)boronic acid (PBI 4452)

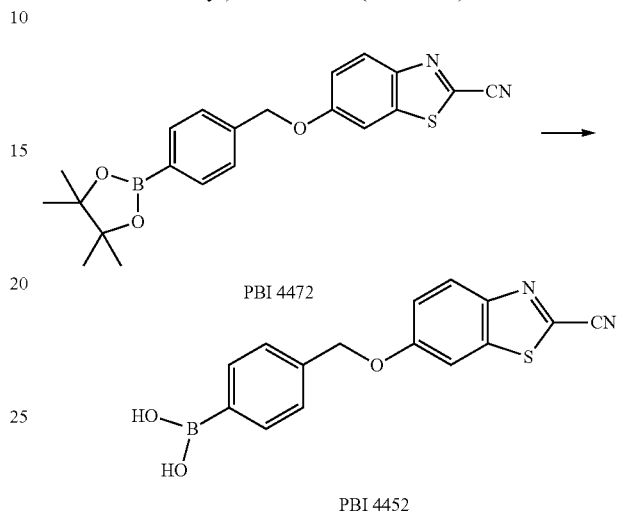

PBI 4452

To a solution of 6-((4-(4,4,5,5-tetramethyl-1,3,2-dioxaborolan-2-yl)benzyl)oxy)benzo[d]thiazole-2-carbonitrile (PBI 4472) (0.26 g, 0.66 mmol) in acetone (40 ml), a suspension of sodium periodate (0.43 g, 1.99 mmol), ammonium acetate (0.11 g, 1.33 mmol) in water (40 ml) was added at room temperature. The thick suspension was allowed to stir at room temperature for 18 hours. All solvent was evaporated, and the residue was dissolved in DMF. The suspension was centrifuged, and the clean solution was purified by prep-HPLC with acetonitrile/10% ammonium acetate to give the product as a white crystal (0.15 g, 72%). $^1$H NMR (300 MHz, DMSO, δ): 8.15 (d, J=9.0 Hz, 1H), 8.04 (s, 2H), 7.97 (d, J=3.0 Hz, 1H), 7.80 (d, J=9.0 Hz, 2H), 7.41 (m, 3H), 5.23 (s, 2H); MS (ESI) m/z 311.1.

Example 3

6-((3-chloro-4-(4,4,5,5-tetramethyl-1,3,2-dioxaborolan-2-yl)benzyl)oxy)-benzo[d]thiazole-2-carbonitrile (PBI 4595)

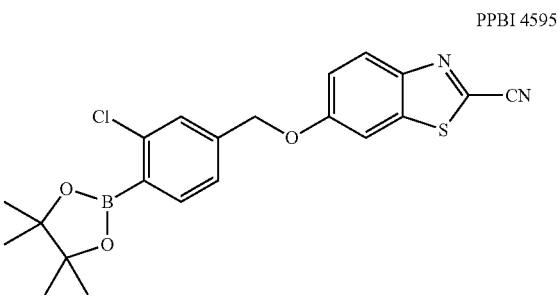 [SMILES: CC1(C)OB(c2ccc(COc3ccc4nc(C#N)sc4c3)cc2Cl)OC1(C)C]

PPBI 4595

This compound was made following the same procedures as PBI 4472 (Example 1).

Example 4

(2-chloro-4-(((2-cyanobenzo[d]thiazol-6-yl)oxy)methyl)phenyl)boronic acid (PBI 4470)

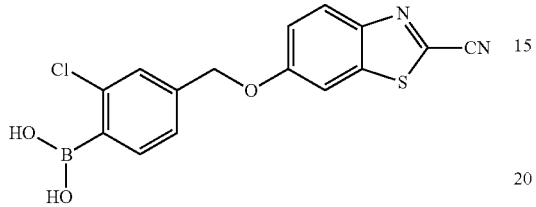

This compound was made following the same procedure as PBI 4452 (Example 2). $^1$H NMR (300 MHz, DMF, δ): 8.43 (s, 2H), 8.22 (d, J=9.0 Hz, 1H), 8.07 (m, 1H), 7.56 (m, 2H), 7.47 (m, 2H), 5.33 (s, 2H); MS (ESI) m/z 345.1.

Example 5

6-((4-(4,4,5,5-tetramethyl-1,3,2-dioxaborolan-2-yl)naphthalen-1-yl)methoxy)benzo[d]thiazole-2-carbonitrile (PBI 4480)

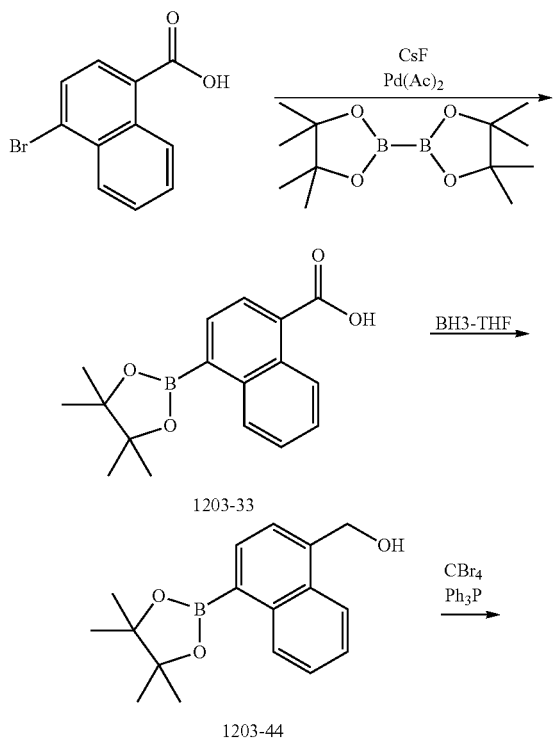

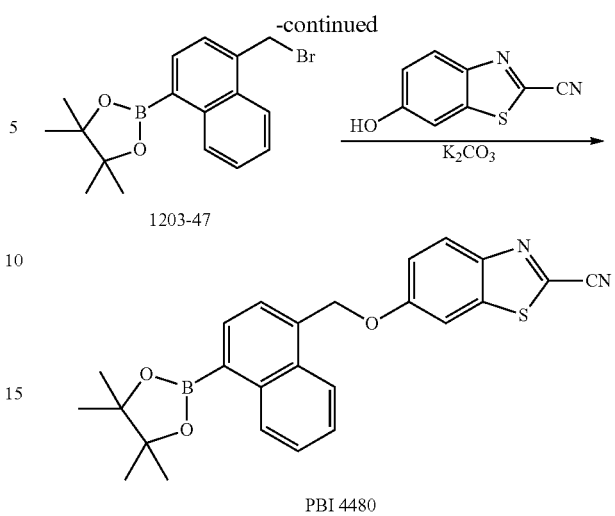

Synthesis of 4-(4,4,5,5-tetramethyl-1,3,2-dioxaborolan-2-yl)-1-naphthoic acid (1203-33)

A mixture of 4-bromo-1-naphthoic acid (4.12 g, 16.43 mmol), bis(pinacolato)diborane (4.38 g, 17.25 mmol), cesium fluoride (7.49 g, 49.28 mmol), triphenylphosphine (0.86 g, 3.29 mmol) in acetonitrile was added palladium acetate (0.37 g, 1.64 mmol). The reaction mixture was refluxed overnight. After cooling down, it was filtered through Celite and extracted with ethyl acetate/water. The organic layer was collected and dried over sodium sulfate. After filtration, solvent was removed and the residue was purified by flash chromatography to give the product as a white solid (2.5 g, 51%). $^1$H NMR (300 MHz, DMSO, δ): 8.76 (m, 1H), 8.69 (m, 1H), 8.02 (m, 2H), 7.61 (m, 1H), 1.28 (s, 12H).

Synthesis of (4-(4,4,5,5-tetramethyl-1,3,2-dioxaborolan-2-yl)naphthalen-1-yl)methanol (1203-44)

4-(4,4,5,5-tetramethyl-1,3,2-dioxaborolan-2-yl)-1-naphthoic acid (2.5 g, 8.39 mmol) was dissolved in anhydrous THF. The solution was cooled down in an ice-water bath. Borane solution (1.00M in THF, 25 ml, 25 mmol) was added dropwise. After addition, the reaction was stirred at room temperature for 4 hours. Methanol (20 ml) was added with ice-water batch to quench the reaction until no gas was produced. The solvent was evaporated, and the residue was extracted with ethyl acetate/water to give the product as a white solid (1.79 g, 75%). $^1$H NMR (300 MHz, CD$_2$Cl$_2$, δ): 8.80 (m, 1H), 8.10 (m, 1H), 8.04 (m, 1H), 7.57 (m, 3H), 5.18 (s, 2H), 1.43 (s, 12H).

Synthesis of 2-(4-(bromomethyl)naphthalen-1-yl)-4,4,5,5-tetramethyl-1,3,2-dioxaborolane (1203-47)

This compound was made following the same procedure as 1203-32 (Example 1). $^1$H NMR (300 MHz, CD$_2$Cl$_2$, δ): 8.82 (m, 1H), 8.19 (m, 1H), 8.00 (m, 1H), 7.60 (m, 3H), 5.02 (s, 2H), 1.43 (s, 12H).

Synthesis of 6-((4-(4,4,5,5-tetramethyl-1,3,2-dioxaborolan-2-yl)naphthalen-1-yl)methoxy)benzo[d]thiazole-2-carbonitrile (PBI 4480)

This compound was made following the same procedure as PBI 4472 (Example 1). $^1$H NMR (300 MHz, CD$_2$Cl$_2$, δ): 8.85

(m, 1H), 8.11 (d, 1H), 8.06 (m, 2H), 7.09 (m, 4H), 7.38 (m, 1H), 5.35 (s, 2H), 1.42 (s, 12H); MS (ESI) m/z 443.2.

Example 6

6-((3-fluoro-4-(4,4,5,5-tetramethyl-1,3,2-dioxaborolan-2-yl)benzyl)oxy)benzo[d]thiazole-2-carbonitrile (PBI 4481)

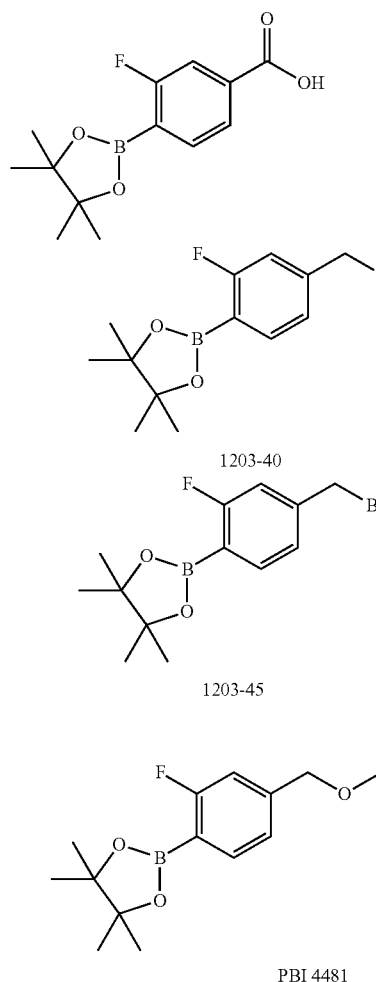

Synthesis of 2-(4-(bromomethyl)-2-fluorophenyl)-4,4,5,5-tetramethyl-1,3,2-dioxaborolane (1203-40)

The compound was made following the same procedure as 1203-44 (Example 5). $^1$H NMR (300 MHz, CD$_2$Cl$_2$, δ): 7.70 (m, 1H), 7.15 (m, 1H), 7.06 (m, 1H), 4.71 (s, 2H), 1.35 (s, 12H); MS (ESI) m/z 253.2.

Synthesis of 2-(4-(bromomethyl)-2-fluorophenyl)-4,4,5,5-tetramethyl-1,3,2-dioxaborolane (1203-45)

The compound was made following the same procedure as 1203-32 (Example 1). $^1$H NMR (300 MHz, CD$_2$Cl$_2$, δ): 7.71 (m, 1H), 7.68 (m, 1H), 7.09 (m, 1H), 4.49 (s, 2H), 1.35 (s, 12H); FNMR: 102.97; MS (ESI) m/z 315.1.

Synthesis of 6-((3-fluoro-4-(4,4,5,5-tetramethyl-1,3,2-dioxaborolan-2-yl)benzyl)oxy)benzo[d]thiazole-2-carbonitrile (PBI 4481)

The compound was made following the same procedure as PBI 4472 (Example 1). $^1$H NMR (300 MHz, CD$_2$Cl$_2$, δ): 8.12 (d, J=9.0 Hz, 1H), 7.77 (m, 1H), 7.45 (d, J=3.0 Hz, 1H), 7.35 (dd, J=3.0 Hz, 9.0 Hz), 7.26 (m, 1H), 7.17 (m, 1H), 5.21 (s, 2H), 1.36 (s, 12H); MS (ESI) m/z 411.2.

Example 7

6-(1-(4-(4,4,5,5-tetramethyl-1,3,2-dioxaborolan-2-yl)phenyl)ethoxy)benzo[d]thiazole-2-carbonitrile (PBI 4513)

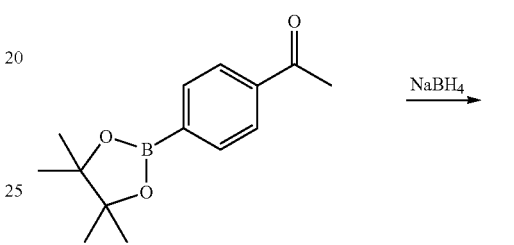

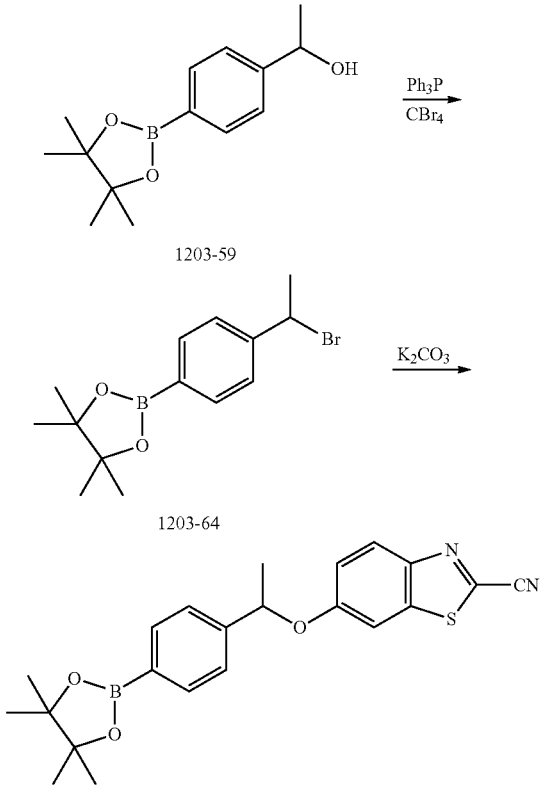

Synthesis of 1-(4-(4,4,5,5-tetramethyl-1,3,2-dioxaborolan-2-yl)phenyl)ethanol (1203-59)

4-acetylphenyl boronic acid (3.0 g, 12.2 mmol) was dissolved in anhydrous ethanol (30 ml) and cooled in an ice/water bath. NaBH$_4$ (1.15 g, 30.5 mmol) was added at once as a solid. After stirring overnight at room temperature, the solution was cooled in an ice-water bath and treated with 1N HCl (20 ml). The mixture was then extracted with ethyl acetate, dried over sodium sulfate, filtered and concentrated under vacuum. The crude product obtained was purified with flash chromatography to give the product as a white solid (2.98 g, 99%). ¹H NMR (300 MHz, CD₂Cl₂, δ): 7.75 (m, 2H), 7.39 (m, 2H), 4.90 (q, J=6.0 Hz), 1.47 (d, J=6.0 Hz), 1.32 (s, 12H).

Synthesis of 2-(4-(1-bromoethyl)phenyl)-4,4,5,5-tetramethyl-1,3,2-dioxaborolane (1203-64)

The compound was made following the same procedure as 1203-32 (Example 1). ¹H NMR (300 MHz, CD₂Cl₂, δ): 7.76 (m, 2H), 7.45 (m, 2H), 5.25 (q, J=6.0 Hz), 2.05 (d, J=6.0 Hz), 1.32 (s, 12H); MS (ESI) m/z 311.2.

Synthesis of 6-(1-(4-(4,4,5,5-tetramethyl-1,3,2-dioxaborolan-2-yl)phenyl)ethoxy)benzo[d]thiazole-2-carbonitrile (PBI 4513)

The compound was made following the same procedure as PBI 4472 (Example 1). ¹H NMR (300 MHz, CD₂Cl₂, δ): 8.03 (m, 1H), 7.76 (m, 2H), 7.44 (m, 2H), 7.28 (m, 2H), 5.43 (q, J=6.0 Hz, 1H), 1.69 (d, J=6.0 Hz, 3H), 1.32 (s, 12H); MS (ESI) m/z 407.2.

Example 8

6-((3-methoxy-4-(4,4,5,5-tetramethyl-1,3,2-dioxaborolan-2-yl)benzyl)oxy)benzo[d]thiazole-2-carbonitrile (PBI 4512)

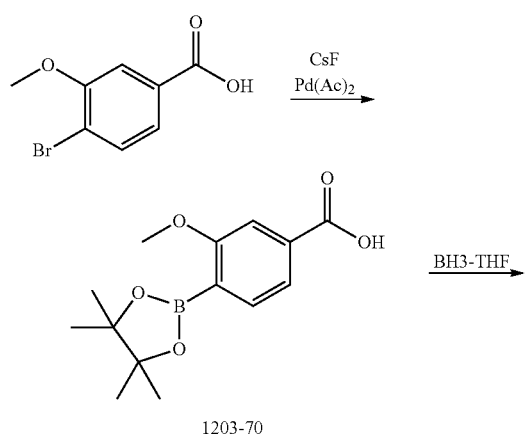

1203-70

1203-79

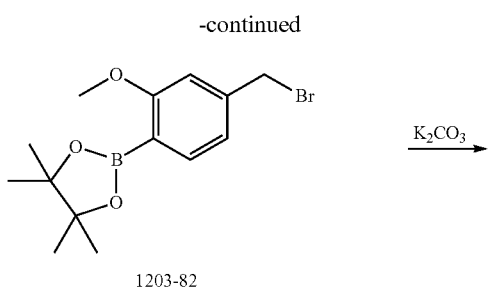

1203-82

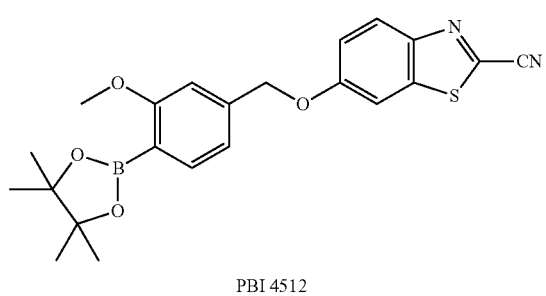

PBI 4512

Synthesis of 3-methoxy-4-(4,4,5,5-tetramethyl-1,3,2-dioxaborolan-2-yl)benzoic acid (1203-70)

The compound was made following the same procedure as 1203-33 (Example 5). ¹H NMR (300 MHz, DMSO, δ): 7.74 (m, 1H), 7.66 (m, 1H), 7.57 (m, 1H), 3.90 (s, 3H), 1.35 (s, 12H); MS (ESI) m/z 277.6.

Synthesis of (3-methoxy-4-(4,4,5,5-tetramethyl-1,3,2-dioxaborolan-2-yl)phenyl)methanol (1203-79)

The compound was made following the same procedure as 1203-44 (Example 5) and used in the next step without purification.

Synthesis of 2-(4-(bromomethyl)-2-methoxyphenyl)-4,4,5,5-tetramethyl-1,3,2-dioxaborolane (1203-82)

The compound was made following the same procedure as 1203-32 (Example 1) and used in the next step without purification.

Synthesis of 6-((3-methoxy-4-(4,4,5,5-tetramethyl-1,3,2-dioxaborolan-2-yl)benzyl)oxy)benzo[d]thiazole-2-carbonitrile (PBI 4512)

The compound was made following the same procedure as 1203-36 (Example 1). ¹H NMR (300 MHz, CD₂Cl₂, δ): 8.11 (d, J=9.0 Hz, 1H), 7.69 (d, J=9.0 Hz, 1H), 7.47 (d, J=3.0 Hz, 1H), 7.35 (m, 1H), 7.04 (m, 1H), 6.98 (m, 1H), 5.20 (s, 2H), 3.84 n (s, 3H), 1.34 (s, 12H).

Example 9

4-(4,4,5,5-tetramethyl-1,3,2-dioxaborolan-2-yl)benzyl (2-cyanobenzo[d]thiazol-6-yl)carbamate (PBI 4579)

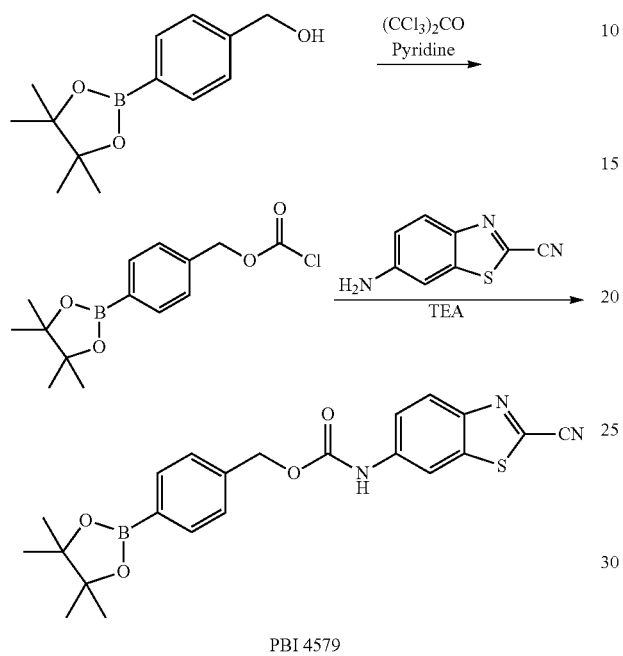

PBI 4579

Triphosgen (0.26 g, 0.77 mmol) and 4-hydroxymethylphenylboronic acid, pinacol ester (0.5 g, 2.14 mmol) were dissolved in THF (20 ml) in an ice-water bath. Pyridine (0.35 ml, 4.28 mmol) was added dropwise, and the reaction mixture was stirred at 0° C. until thin layer chromatography showed the disappearance of starting material. After bring the temperature to room temperature, the reaction mixture was extracted with dichloromethane/water. The organic layer was collected and dried over sodium sulfate. After filtration, solvent was removed and the residue was purified by flash chromatography to give the product as a white solid (0.1 g, 11%). $^1$H NMR (300 MHz, CD$_2$Cl$_2$, δ): 8.43 (m, 1H), 8.10 (m, 1H), 7.78 (m, 2H), 7.41 (m, 2H), 7.26 (m, 1H), 5.25 (s, 2H), 1.32 (s, 12H); MS (ESI) m/z 436.1.

Example 10

6-((4-(5,5-dimethyl-1,3,2-dioxaborinan-2-yl)benzyl)oxy)benzo[d]thiazole-2-carbonitrile (PBI 4578)

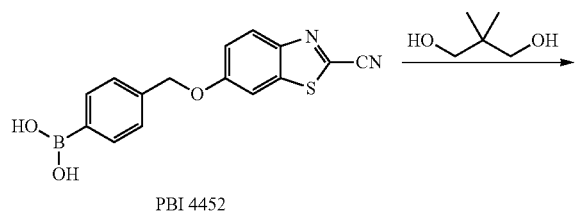

PBI 4452

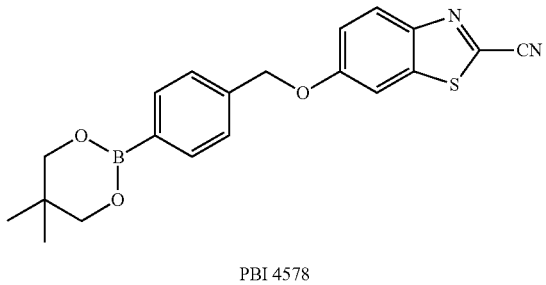

PBI 4578

A mixture of PBI 4452 (Example 2) (20 mg, 0.065 mmol) and neopentyl glycol (34 mg, 0.32 mmol) in toluene (50 ml) was heated to reflux in Dean-Stark apparatus. The reaction was cooled down after 16 hours. Toluene was evaporated, and the residue was purified by flash chromatography to give the product as a white solid (10 mg, 41%). $^1$H NMR (300 MHz, CD$_2$Cl$_2$, δ): 8.11 (d, J=9.0 Hz, 1H), 7.82 (d, J=6.0 Hz, 2H), 7.46 (m, 3H), 7.34 (dd, J=6.0 Hz, 3.0 Hz, 1H), 5.20 (s, 2H), 3.78 (s, s, 4H), 1.03 (s, 6H).

Example 11

(E)-6-((3-(4,4,5,5-tetramethyl-1,3,2-dioxaborolan-2-yl)allyl)oxy)-benzo[d]thiazole-2-carbonitrile (PBI 4458)

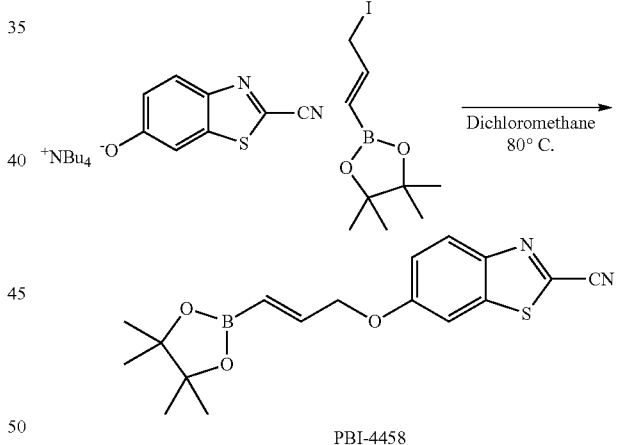

PBI-4458

A reaction vial was charged with tetrabutylammonium 2-cyanobenzo[d]thiazol-6-olate (209 mg, 1.19 mmol), (E)-2-(3-iodoprop-1-en-1-yl)-4,4,5,5-tetramethyl-1,3,2-dioxaborolane (386 mg, 1.31 mmol) and 15 mL of dry dichloromethane. The vial was sealed, and the solution was heated in an oil bath at 80° C. overnight (~16 hours). The crude reaction mixture was added to 1 gram of celite, and the solvent was evaporated under vacuum. The product was purified by silica gel chromatography using an increasing gradient of ethyl acetate in dichloromethane as eluent. This gave 166 mg of (E)-6-((3-(4,4,5,5-tetramethyl-1,3,2-dioxaborolan-2-yl)allyl)oxy)benzo[d]thiazole-2-carbonitrile as a colorless oil that crystallized to a white solid upon standing at ambient temperature.

Example 12

Synthesis of 8-benzyl-2-(furan-2-ylmethyl)-6-phenyl-3-((4-(4,4,5,5-tetramethyl-1,3,2-dioxaborolan-2-yl)benzyl)oxy)imidazo[1,2-a]pyrazine

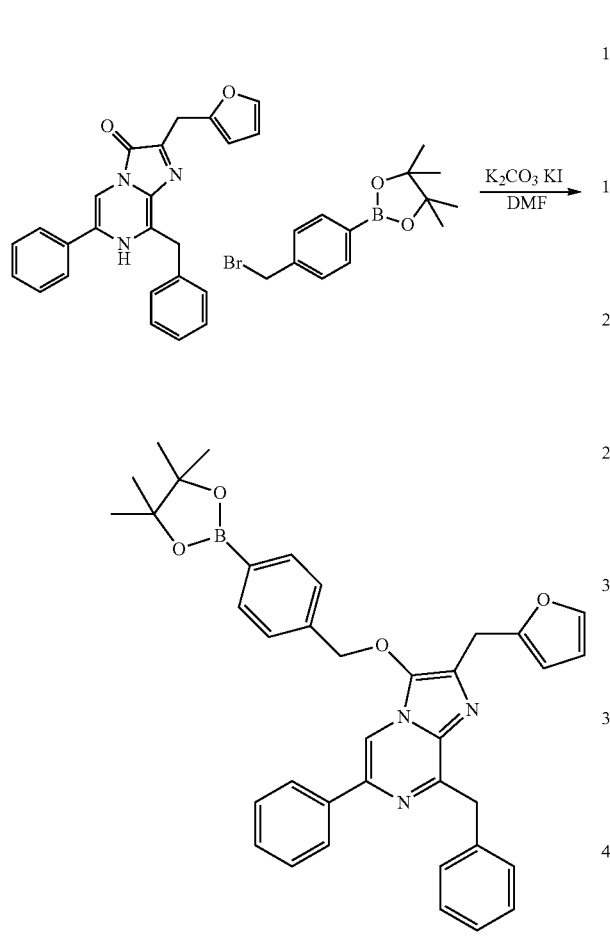

Synthesis of 8-benzyl-2-(furan-2-ylmethyl)-6-phenyl-3-((4-(4,4,5,5-tetramethyl-1,3,2-dioxaborolan-2-yl)benzyl)oxy)imidazo[1,2-a]pyrazine (4759). To a solution of 8-benzyl-2-(furan-2-ylmethyl)-6-phenylimidazo[1,2-a]pyrazin-3 (7H)-one (50 mg, 0.13 mmol) was added 2-(4-(bromomethyl)phenyl)-4,4,5,5-tetramethyl-1,3,2-dioxaborolane (47 mg, 0.16 mmol), potassium carbonate (27 mg, 0.20 mmol) and potassium iodide (33 mg, 0.20 mmol). The reaction mixture was stirred at room temperature for 1 h and heat to 40° C. until HPLC shows the completion of the reaction. After cooling down, the reaction mixture was extracted with ethyl acetate/water. The organic layer was collected and dried over magnesium sulfate. After evaporation, the residue was purified with flash chromatography to give the product as yellow solid (30 mg, 49%). $^1$H NMR (300 MHz, CD$_2$Cl$_2$, δ): 7.79-7.23 (m, 18H), 7.32 (d, J=6.0 Hz, 2H), 5.11 (s, 2H), 4.53 (s, 2H), 4.15 (s, 2H), 1.53 (s, 12H); MS (ESI) m/z 597.41.

Prophetic Example 13. Synthesis of 8-benzyl-2-(furan-2-ylmethyl)-6-phenyl-2-(4-(4,4,5,5-tetramethyl-1,3,2-dioxaborolan-2-yl)benzyl)imidazo[1,2-a]pyrazin-3(2H)-one

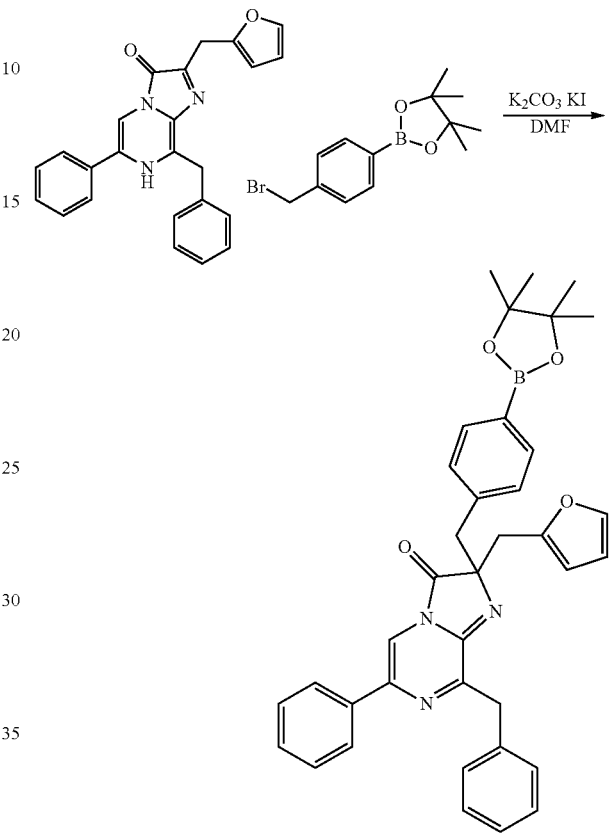

Synthesis of 8-benzyl-2-(furan-2-ylmethyl)-6-phenyl-2-(4-(4,4,5,5-tetramethyl-1,3,2-dioxaborolan-2-yl)benzyl)imidazo[1,2-a]pyrazin-3(2H)-one. To a solution of 8-benzyl-2-(furan-2-ylmethyl)-6-phenylimidazo[1,2-a]pyrazin-3 (7H)-one, 2-(4-(bromomethyl)phenyl)-4,4,5,5-tetramethyl-1,3,2-dioxaborolane, potassium carbonate and potassium iodide (33 mg, 0.20 mmol) is added. The reaction mixture is stirred at room temperature and is heated to 40° C. until HPLC shows the completion of the reaction.

Example 14

Generation of Bioluminescence Upon Treatment with Peroxide

In this example, luciferin borates were incubated with hydrogen peroxide, and luciferin generation was measured using a light reaction catalyzed by luciferase. An increase in light output (bioluminescence) as a result of treatment of the luciferin borates with hydrogen peroxide indicates generation of luciferin as a result of the reaction with hydrogen peroxide.

1 M phosphate solutions (either 6.8 g of KH$_2$PO$_4$ (Fisher) or 11.4 g of K$_2$HPO$_4$ (Sigma) were dissolved in Nanopure water to 1 M) were diluted 1:5 with Nanopure water to produce 200 mM phosphate solutions. 200 mM phosphate buffers at pH 6.87, 7.41, 7.73, 8.04, and 9.18 were prepared. 4 mg/ml solutions of PBI 3048, 4013, 4424 and 4425 (FIG. 1) in DMSO (Fluka 41641) were made from solid powder.

Into two 96-well white, solid bottom luminometer plates (Promega Z3291) (labeled "A" and "B"), 50 µl of 200 mM phosphate buffer pH 6.87 was added to wells A1-H2; 50 µl of 200 mM phosphate pH 7.41 was added to wells A3-H4; 50 µl of 200 mM phosphate buffer pH 7.73 was added to wells A5-H6; 50 µl of 200 mM phosphate buffer pH 8.04 was added to wells A7-H8; and 50 µl of 200 mM phosphate buffer pH 9.18 was added to wells A9-H10.

50 µl of 4 mg/ml PBI 4013 in DMSO was diluted to 1.25 ml with Nanopure water, and 25 µl added to wells A1-D10 of plate A. 50 µl of 4 mg/ml PBI 4424 was diluted to 1.25 ml with Nanopure water, and 25 µl added to E1-H10 of plate A. 50 µl of 4 mg/ml PBI 3048 was diluted to 1.25 ml with Nanopure water, and 25 µl added to A1-D10 of plate B. 50 µl of 4 mg/ml PBI 4425 was diluted to 1.25 ml with Nanopure water, and 25 µl added to E1-H10 of plate B. 25 µl of Nanopure water was added to rows A and E of both plates. 17 µl of Nanopure water was added to rows B and F of both plates; and 8 µl of Nanopure water was added to rows C and G of both plates A hydrogen peroxide solution (30% hydrogen peroxide, Sigma H1009-5 ml) was diluted to 60 µM hydrogen peroxide with Nanopure water, and 25 µl of the 60 µM hydrogen peroxide was added to rows D and H of both plates; 17 µl of 60 µl M hydrogen peroxide was added to rows C and G of both plates; and 8 µl of 60 µl hydrogen peroxide was added to rows B and F of both plates. Both plates A and B were then gently mixed for 70 minutes.

A bottle of Reconstitution Buffer with Esterase (Promega V144B) was thawed and used to reconstitute a Luciferin Detection Reagent (Promega V859B) to create a reconstituted Luciferin Detection Reagent ("LDR"). 15 ml of 1 M HEPES buffer, pH 7.5 was mixed with 25 ml of the LDR, and 80 µl added to wells A1-H10 of two new luminometer plates ("R1" and "R2").

Following incubation, 20 µl of the contents of wells A1-H10 of plate A was transferred to the same wells in plate R1, and 20 µl of A1-H10 of plate B was transferred to the same wells in plate R2. Plate R1 and R2 were then incubated at room temperature for 15 minutes, and bioluminescence was measured with a GloMax® luminometer (Promega Corp).

Bioluminescence from duplicate wells was averaged, and the average relative light units (RLUs) from samples containing peroxide were compared to those from the samples not containing peroxide incubated at the same pH (Table 1).

TABLE 1

|  | $H_2O_2$ (µM) | pH 6.87 | pH 7.41 | pH 7.73 | pH 8.04 | pH 9.18 |
| --- | --- | --- | --- | --- | --- | --- |
| PBI 4013 | 0 | 421,702 | 469,602 | 573,023 | 585,008 | 700,831 |
|  | 5 | 580,978 | 760,900 | 1,089,717 | 1,534,619 | 3,678,815 |
|  | 10 | 680,475 | 1,020,315 | 1,634,356 | 2,485,677 | 5,433,577 |
|  | 15 | 793,789 | 1,282,281 | 2,209,227 | 3,373,538 | 7,062,631 |
| PBI 4424 | 0 | 17,522 | 16,181 | 17,087 | 18,602 | 17,794 |
|  | 5 | 18,952 | 17,583 | 18,681 | 20,935 | 22,309 |
|  | 10 | 19,891 | 17,508 | 19,298 | 20,554 | 20,333 |
|  | 15 | 20,263 | 19,332 | 25,729 | 21,486 | 20,453 |
| PBI 3048 | 0 | 392,535 | 418,478 | 470,830 | 561,030 | 819,156 |
|  | 5 | 521,375 | 794,181 | 1,200,842 | 1,831,013 | 3,834,248 |
|  | 10 | 717,216 | 1,302,514 | 2,057,780 | 3,137,287 | 6,426,397 |
|  | 15 | 833,785 | 1,709,044 | 2,713,251 | 4,193,451 | 7,447,757 |
| PBI 4425 | 0 | 10,464 | 10,266 | 9,302 | 10,312 | 9,428 |
|  | 5 | 13,296 | 14,549 | 13,739 | 15,130 | 19,728 |
|  | 10 | 14,491 | 14,768 | 17,086 | 19,258 | 26,859 |
|  | 15 | 14,105 | 14,725 | 15,789 | 18,905 | 24,236 |

As can be seen in Table 1, the light emitted from two of the compounds, PBI 4013 and PBI 3048, increased strongly upon addition of hydrogen peroxide at all pH values. However, greater light signal increases were seen as the pH increased from pH 6.87 to pH 9.18. The light signal increases measured for the other two compounds, PBI 4425 and PBI 4424, were much smaller upon hydrogen peroxide addition than was seen for PBI 3048 or PBI 4013.

These results indicate that luciferin borates can be used to detect and measure hydrogen peroxide at low levels, but that small structural changes in the particular compounds can have very dramatic effects on the increase of the relative strength of the light signal. In addition, these results indicate that a stronger light signal is obtained from reactions of luciferin borates with hydrogen peroxide at pH values above pH 8.0.

Example 15

Comparison of Light Generation from Compounds of the Present Invention Following Incubation with Hydrogen Peroxide In this experiment, various compounds were tested for their ability to detect hydrogen peroxide in different pH solutions. Several compounds are shown to give much better signal strength and signal to background ratios than PBI 3048 (Example 23). 4 mg/ml solutions of compounds PBI 4480, 4481, 4452, 4470, 4472, 3048 (FIGS. 1 and 2) were made by dissolving them in DMSO (Fluka 41641). 30 µl of the compound solutions was diluted to 1.5 ml with Nanopure water, and 50 µl aliquots added as follows into a white, 96-well luminometer plate: PBI 4481, row A1-12; PBI 4480, row B1-12; PBI 4452, row C1-12; PBI 3048, row D1-12; PBI 4472, row E1-12 and PBI 4470, row F1-12.

25 µl of 200 mM TRIS buffer, pH 7.6 was added to wells A1-F4, 25 µl of 200 mM TRIS buffer, pH 8.8 was added to wells A5-F8, and 25 µl of 200 mM Tris buffer, pH 10.4 was added A9-F10.

30% hydrogen peroxide (Sigma H 1009-5 ml) was diluted to 40 µM in Nanopure water, and 25 µl added to columns 3, 4, 7, 8, 11 and 12 of the plate. 25 µl water was added to columns 1, 2, 5, 6, 9, and 10 of the plate, and the plate incubated at room temperature for 60 minutes.

A conversion solution was made by mixing 100 µl of 100 mM D-cysteine, 1 ml Tris Buffer pH 8.8 and 8.9 ml nanopure water. After mixing, 80 µl of the solution was added to wells A1-F12 of a new luminometer plate.

After incubation, 20 µl of sample from wells A1-F12 of the first plate was transferred to the same well in the new luminometer plate. The new plate was incubated at room temperature for 5 minutes, 100 µl of LDR (Example 23) was added to wells A1-F12, and bioluminescence detected on a Glo Max® luminometer (Promega).

The RLUs for the duplicate wells were averaged. The averages for the wells containing hydrogen peroxide were compared to the wells without hydrogen peroxide at the same pH (Table 2). BZT is used to designate benzothiazole derivatives of the compounds.

TABLE 2

|  |  | pH 7.6 | | pH 8.8 | | pH 10.4 | |
|---|---|---|---|---|---|---|---|
|  |  | No H$_2$O$_2$ | With H$_2$O$_2$ | No H$_2$O$_2$ | With H$_2$O$_2$ | No H$_2$O$_2$ | With H$_2$O$_2$ |
| BZT Borates | PBI 4452 | 607,036 | 1,182,338 | 632,327 | 2,790,924 | 921,935 | 14,577,312 |
|  | PBI 4470 | 492,941 | 701,300 | 468,729 | 1,525,058 | 819,416 | 13,391,102 |
| BZT Borate Esters | PBI 4472 | 102,925 | 1,854,434 | 163,710 | 5,175,361 | 337,921 | 8,159,216 |
|  | PBI 4481 | 124,246 | 873,626 | 135,530 | 2,854,279 | 230,459 | 7,474,603 |
|  | PBI 4480 | 146,664 | 657,132 | 179,821 | 1,563,422 | 265,315 | 5,295,463 |
| Luciferin Borate | PBI 3048 | 569,141 | 1,726,143 | 558,869 | 2,499,869 | 558,333 | 3,768,437 |

The Signal to Background (S/B) ratio is used to compare assay reagents with very difference signal strengths. An assay with a higher S/B ratio is often considered a better assay than one with a smaller S/B ratio (with all other factors being relatively equal). The Signal (with peroxide) to Background (no peroxide) values for this Example are shown in Table 3.

TABLE 3

Signal to Background Ratios

|  |  | pH 7.6 | pH 8.8 | pH 10.4 |
|---|---|---|---|---|
| BZT Borates | PBI 4452 | 1.9 | 4.4 | 15.8 |
|  | PBI 4470 | 1.4 | 3.3 | 16.3 |
| BZT Borate Esters | PBI 4472 | 18.0 | 31.6 | 24.1 |
|  | PBI 4481 | 7.0 | 21.1 | 32.4 |
|  | PBI 4480 | 4.5 | 8.7 | 20.0 |
| Luciferin Borate | PBI 3048 | 3.0 | 4.5 | 6.7 |

Even though PBI 4452 and 4470 are borates, they both produce greater signals with peroxide at pH 10.4 and have a greater S/B ratio at that pH than PBI 3048. This property of the compounds can make them more useful in measuring hydrogen peroxide generated in vitro in enzymatic reactions. On the other hand, the borate esters (PBI 4472, 4481 and 4480) give higher S/B ratios at lower pH than either class of borates suggesting that they may perform better in experiments using live mammalian cells in culture where cells cannot be grown at a pH of pH 10.4. In addition, although they generate a somewhat lower total signal when compared to the BZT borates under some conditions, the borate esters generate an excellent signal to background that could be used if signal strength is not minimal.

Example 16

Detection of Reactive Oxygen Generation Using Luciferin Borates

In this example, various compounds shown to react with hydrogen peroxide were incubated with cells treated with menadione and 4-aminobiphenyl, two compounds that can generate reactive oxygen species (ROS). Menadione causes the direct production of reactive oxygen within the cell and is a very strong inducer of a ROS effect (Sun, J S et. al. Cell Mol Life Sci (1997) vol 53 pp 967-76). 4-aminobiphenyl is believed to require metabolic conversion to a quinine-like structure before being able to induce the formation of a ROS (Makena, P and Chung, K T. Environ. Mol. Mutagen. (2007), vol 48, pp 404-413). One of the borate compounds, PBI 4458, has been shown to give a much stronger signal under conditions that generate reactive oxygen within the cell. This example demonstrates: 1) a method to detect the formation of reactive oxygen species in cells upon application of various treatments using the compounds of the present invention, and 2) the method of 1) can be used to detect reactive species in both attached (e.g., HepG2) and suspension (e.g., Jurkat) cell lines.

A 40 mM solution of 4-aminobiphenyl (Sigma A2898-1g) was made by dissolving 2.5 mg in 375 μl of DMSO (Fluka) to create a 40 mM solution. 50 μl of 4 mg/ml PBI 4458 in DMSO was diluted to 1 ml with HBSS buffer (Invitrogen), and 100 μl added to wells A1 and A2 of a microtiter plate. A 10 μl sample of 40 mM 4-aminobiphenyl was mixed with 190 μl of the remaining PBI 4458 in HBSS, and 60 μl added to wells B1 and B2 and 30 μl to wells C1 and C2. A 10 μl sample of 40 mM menadione in DMSO was mixed with 190 μl of the remaining PBI 4458 in HBSS, and 60 μl added to wells D1 and D2 and 30 μl to E1 and E2. The volume in wells B1 to E2 was then adjusted to 100 μl by addition of remaining PBI 4458 in HBSS.

50 μl of 4 mg/ml PBI 4480 in DMSO was diluted to 1 ml with HBSS buffer, and 100 μl placed in wells A3 and A4 of the microtiter plate. A 10 μl sample of 40 mM 4 aminobiphenyl was mixed with 190 μl of the remaining PBI 4480 in HBSS, and 60 μl added to wells B3 and B4 and 30 μl to wells C3 and C4. A 10 μl sample of 40 mM menadione in DMSO was mixed with 190 μl of the remaining PBI 4480 in HBSS, and 60 μl added to wells D3 and D4 and 30 μl added to wells E3 and E4. The volume in wells B3 to E4 was then adjusted to 100 μl by addition of left over PBI 4480 in HBSS.

50 μl of 4 mg/ml PBI 3048 in DMSO was diluted to 1 ml with HBSS, and 100 μl added to wells A5 and A6 of the microtiter plate. A 10 μl sample of 40 mM 4 aminobiphenyl was mixed with 190 μl of the remaining PBI 3048 in HBSS, and 60 μl added to wells B5 and B6 and 30 μl added to wells C5 and C6. A 10 μl sample of 40 mM menadione in DMSO was mixed with 190 μl of the remaining PBI 3048 in HBSS, and 60 μl added to wells D5 and D6 and 30 μl added to wells E5 and E6. The volume in wells B5 to E6 was then adjusted to 100 μl by addition of the remaining PBI 3048 in HBSS.

Two cell culture plates were seeded with cells resuspended in HBSS. One plate contained 20,000 Jurkat cells/well in wells A1-H6. The other plate contained 20,000 HepG2 cells/well in wells A1-H6. Both plates were incubated overnight in DMEM with 10% fetal bovine serum (FBS). The media from the HepG2 cells was removed, discarded, and replaced with 50 μl of HBSS. A 50 μl sample of wells A1-H6 from the plate with the various PBI compounds was transferred to the corresponding wells in the two cell culture plates, and incubated for 60 minutes in a 37° C., 5% CO2 incubator.

50 μl of LDR (Example 23) and 25 μl of 1 mM D-cysteine in 100 mM HEPES buffer, pH 7.5 was added to all wells of a new luminometer plate. After incubation, a 25 μl sample of wells A1-H6 containing Jurkat cells was added to wells A1-H6 of the new luminometer plate, and a 25 μl sample of wells A1-H6 containing HepG2 cells was added to wells A7-H12 of the new luminometer plate. The plate was incubated at room temperature for 15 minutes, and bioluminescence detected on a GloMax® luminometer.

The bioluminescence from the duplicate samples was averaged and compared to the values of the cells in A row (Table 4).

TABLE 4

|  | Jurkat | | | HepG2 | | |
| --- | --- | --- | --- | --- | --- | --- |
|  | PBI 4458 | PBI 4480 | PBI 3048 | PBI 4458 | PBI 4480 | PBI 3048 |
| No Effector | 174,206 | 34,646 | 413,753 | 117,111 | 19,627 | 407,917 |
| 600 μM 4ABP | 195,096 | 29,277 | 366,188 | 169,952 | 21,023 | 383,471 |
| 300 μM 4ABP | 213,059 | 29,810 | 363,182 | 163,031 | 20,574 | 364,353 |
| 600 μM Menadione | 895,269 | 27,535 | 403,013 | 728,404 | 20,509 | 408,177 |
| 300 μM Menadione | 742,717 | 29,806 | 434,344 | 622,230 | 20,788 | 426,802 |

The values for the different levels of 4-aminobiphenyl and menadione with PBI 4458 are above those for the cells that were not given any effector, as was expected. Also, the magnitude of the response for menadione was much greater than for 4-aminobiphenyl. The values for PBI 4480 and PBI 3048 do not show as clear of a response to the menadione or 4 aminobiphenyl. The reduced response is not surprising since these compounds showed a less then strong response to direct hydrogen peroxide addition as seen in Example 23.

These results indicate that PBI 4458 allows sensitive detection of an agent that generates reactive oxygen in mammalian cells. In addition, the results clearly demonstrate that not all borate analogs attached to a benzothiazole or luciferin will generate signals when used with cells. In fact, some of the compounds generate signals with cells in buffer that may be too weak for reliable detection of the effects of compounds on reactive oxygen generation in mammalian cells in culture.

Example 17

Buffer Effects on Luciferin Generation

In this example, borate compounds of the present invention were incubated in various buffers to demonstrate that improved signal strength can be obtained using the proper buffer. In addition, the example demostrates that signal generation in two buffers, DMEM and HBSS buffer, worked well with mammalian cells. Some compounds generated greatly stronger signals in DMEM than in HBSS even though both are formulated to have the same pH value thus demonstrating that the particular compounds of the present invention may be very advantageous to use with mammalian cells in a media such as DMEM.

a. Demonstration of Signal Strength Differences Due to Reaction pH and Buffer Composition.

A 30 μl sample of 4 mg/ml PBI 4458 in DMSO was diluted to 1.5 ml with Nanopure water, and 50 μl added to wells A1-12 and E1-12 of a microtiter plate. A 30 μl sample of 4 mg/ml PBI 4472 in DMSO was diluted to 1.5 ml with Nanopure, and 50 μl added to wells B1-12 and F1-12 of the plate. A 30 μl sample of 4 mg/ml PBI 4480 in DMSO was diluted to 1.5 ml with Nanopure water, and 50 μl added to wells C1-12 and G1-12 of the plate. A 30 μl sample of 4 mg/ml PBI 4481 in DMSO was diluted to 1.5 ml with Nanopure water, and 50 μl added to wells D1-12 and H1-12 of the plate. To the plate, a 50 μl sample of 200 mM $KHPO_4$, pH 7.4 was added to wells A1-D4; 50 μl 200 mM Tris buffer, pH 7.4 was added to wells A5-D8; 50 μl 250 mM HEPES buffer, pH 7.5 was added to wells A9-D12; 50 μl 200 mM $KHPO_4$ buffer, pH 9.2 was added to wells E1-H4; 50 μl 250 mM Tris buffer, pH 10.4 was added to wells E5-H8; and 50 μl 100 mM CAPS buffer, pH 10.4 was added to wells E9-H12.

A sample of hydrogen peroxide (30%, Sigma, H1009-5 ml) was diluted to 10 μM with Nanopure water, and 100 μl added to columns 3, 4, 7, 8, 11, 12 wells A-H of the plate. 100 μl Nanopure water was added to columns 1, 2, 5, 6, 9 and 10 of the plate. The plate was incubated at room temperature for 15 minutes.

A conversion solution was made by mixing 5 ml of 1 M HEPES buffer, pH 7.5, 4.9 ml of Nanopure water and 100 μl of 100 mM D-cysteine (in Nanopure water), and 25 p. 1 added to all wells of a luminometer plate.

After incubation, 25 μl of sample from all wells in the plate was transferred and mixed into the corresponding wells in the luminometer plate, incubated 2-3 minutes at room temperature, and 50 μl LDR (Example 23) added. The luminometer plate was incubated for 15 minutes at room temperature, and bioluminescence detected on a GloMax® luminometer.

Additional samples were taken at 60 and 105 minutes and added to a fresh luminometer plates containing 25 μl of conversion solution in all wells. The plates were then incubated for 15 minutes at room temperature, and bioluminescence detected as previously described.

The RLUs from duplicate wells were averaged, and the values from the samples containing hydrogen peroxide were compared to the corresponding average of the samples that did not contain hydrogen peroxide (Tables 5, 7 and 9), and the signal to background determined (Tables 6, 8 and 10).

TABLE 5

| Net Average Signals at 15 Minutes | | | | | | |
| --- | --- | --- | --- | --- | --- | --- |
|  | $KPO_4$ Ph 7.4 | Tris pH 7.4 | HEPES pH 7.5 | $KPO_4$ pH 9.2 | TRIS pH 10.4 | CAPS pH 10.4 |
| PBI 4458 | 148,190 | 150,205 | 117,752 | 937,111 | 2,348,900 | 4,577,774 |
| PBI 4472 | 43,867 | 121,480 | 58,399 | 400,087 | 1,530,303 | 3,154,440 |
| PBI 4480 | 3,538 | 7,845 | −234 | 37,330 | 743,427 | 1,799,015 |
| PBI 4481 | 16,032 | 29,382 | 15,697 | 189,573 | 1,467,615 | 3,139,869 |

TABLE 6

| Signal to Background Ratios at 15 Minutes | | | | | | |
| --- | --- | --- | --- | --- | --- | --- |
|  | $KPO_4$ pH 7.4 | Tris pH 7.4 | HEPES pH 7.5 | $KPO_4$ pH 9.2 | TRIS pH 10.4 | CAPS pH 10.4 |
| PBI 4458 | 2.2 | 2.2 | 2.0 | 6.4 | 15.2 | 13.2 |
| PBI 4472 | 3.1 | 6.6 | 3.9 | 11.0 | 32.9 | 17.0 |
| PBI 4480 | 1.1 | 1.2 | 1.0 | 1.7 | 11.1 | 12.1 |
| PBI 4481 | 1.5 | 1.9 | 1.4 | 4.7 | 23.2 | 15.0 |

TABLE 7

Net Average Signals at 60 Minutes

| | KPO$_4$ pH 7.4 | Tris pH 7.4 | HEPES pH 7.5 | KPO$_4$ pH 9.2 | TRIS pH 10.4 | CAPS pH 10.4 |
|---|---|---|---|---|---|---|
| PBI 4458 | 615,057 | 626,927 | 494,958 | 2,490,775 | 3,795,644 | 5,831,485 |
| PBI 4472 | 102,614 | 371,397 | 159,982 | 781,296 | 3,777,236 | 5,425,701 |
| PBI 4480 | 38,198 | 61,031 | 29,727 | 218,078 | 1,903,885 | 4,256,769 |
| PBI 4481 | 48,355 | 111,440 | 56,121 | 494,981 | 2,780,433 | 4,514,998 |

TABLE 8

Signal to Background Ratios at 60 Minutes

| | KPO$_4$ pH 7.4 | Tris pH 7.4 | HEPES pH 7.5 | KPO$_4$ pH 9.2 | TRIS pH 10.4 | CAPS pH 10.4 |
|---|---|---|---|---|---|---|
| PBI 4458 | 4.5 | 4.6 | 4.5 | 9.5 | 19.4 | 12.1 |
| PBI 4472 | 4.9 | 13.2 | 8.0 | 14.7 | 34.2 | 15.4 |
| PBI 4480 | 1.6 | 2.0 | 1.7 | 3.6 | 17.9 | 14.7 |
| PBI 4481 | 2.2 | 3.5 | 2.5 | 8.3 | 27.8 | 15.6 |

TABLE 9

Net Average Signals at 105 Minutes

| | KPO$_4$ pH 7.4 | Tris pH 7.4 | HEPES pH 7.5 | KPO$_4$ pH 9.2 | TRIS pH 10.4 | CAPS pH 10.4 |
|---|---|---|---|---|---|---|
| PBI 4458 | 1,297,857 | 1,274,061 | 1,033,511 | 4,925,484 | 5,482,012 | 8,063,108 |
| PBI 4472 | 168,787 | 658,967 | 259,725 | 1,380,626 | 6,279,007 | 7,554,957 |
| PBI 4480 | 86,881 | 162,663 | 75,066 | 587,867 | 3,541,742 | 7,150,225 |
| PBI 4481 | 108,403 | 245,489 | 111,757 | 974,784 | 4,441,956 | 6,646,007 |

TABLE 10

Signal to Background Ratios at 105 Minutes

| | KPO$_4$ pH 7.4 | Tris pH 7.4 | HEPES pH 7.5 | KPO$_4$ pH 9.2 | TRIS pH 10.4 | CAPS pH 10.4 |
|---|---|---|---|---|---|---|
| PBI 4458 | 5.4 | 6.0 | 5.7 | 9.1 | 15.7 | 9.6 |
| PBI 4472 | 5.3 | 13.6 | 8.2 | 14.6 | 26.5 | 11.3 |
| PBI 4480 | 1.9 | 2.6 | 2.3 | 5.1 | 17.5 | 12.6 |
| PBI 4481 | 2.7 | 4.4 | 3.0 | 7.7 | 24.2 | 12.3 |

As seen previously, the bioluminescence signal strength is greater at higher pH values, but there is variation in the signal strength at a particular pH value dependent upon the buffer. For example, even though the buffer pH is nearly identical for the reactions performed using the buffers KPO$_4$, pH 7.4, Tris, pH 7.4 and HEPES, pH 7.5, the net signals seen for PBI 4472 at 105 minutes are different resulting in different signal to background values (5.3, 13.6 and 8.2 for PBI 4472 at 105 minutes in KPO$_4$, Tris pH 7.4, and HEPES pH 7.5, respectively).

B. Signal Differences in Mammalian Cell Culture Media Versus a Physiological Buffer A 100 µl sample of 4 mg/ml DMSO solution of PBI 4458 was diluted to 500 µl with HBSS buffer (Invitrogen 14025-092), and 50 µl added to wells A1-A9 of a fresh microtiter plate ("DISP"). 100 µl 4 mg/ml DMSO solution of PBI 4472 was diluted to 500 µl with HBSS, and 50 µl added to wells E1-E9. 90 µl HBSS was added to wells A1-B9 of two new microtiter plates labeled "RT" and "37C". 90 µl DMEM was added to wells C1-D9 of both plates.

A sample of 30% hydrogen peroxide (Sigma H1009-5 ml) was diluted to 1 mM with Nanopure water, and 7.5 µl 1 mM hydrogen peroxide diluted to 1.5 ml with HBSS, and 90 µl added to wells A4-B6 of plates RT and 37° C. 15 µl 1 mM hydrogen peroxide was diluted to 1 mM with HBSS, and 90 µl added to wells A7-B9 of both plates. 90 µl of HBSS was added to wells A1-B3, and 90 µl of DMEM added to wells C1-D3 of both plates. 7.5 µl 1 mM hydrogen peroxide was diluted to 1.5 ml with DMEM, and 90 µl added to wells C4-D6 of both plates. 15 µl 1 mM hydrogen peroxide was diluted to 1.5 ml with DMEM and 90 µl added to wells C7-D9 of both plates.

10 µl samples of row A of plate "DISP" was transferred to rows A and C of plates RT and 37° C., and 10 µl of row B of plate "DISP" transferred to rows B and D of plates RT and 37° C. The 37° C. plate was incubated at 37° C., 5% CO$_2$, with plate RT incubated at room temperature. Both plates were incubated for 30 minutes.

A conversion solution was made by mixing 7.5 ml of 1 M HEPES, pH 8.0, 7.4 ml Nanopure water and 100 µl 100 mM D cysteine. After mixing, 75 µl was added to all wells of a new luminometer plate.

After incubation, 25 µl from wells A1-D9 of the 37° C. plate was transferred to wells E1-H9 of the new luminometer plate, 25 µl of wells A1-D9 of the RT plate was transferred to wells A1-D9 of new luminometer plate, and the plate incubated at room temperature for 2-3 minutes. A 100 µl sample of LDR (Example 23) was added to wells A1-H9, incubated for 15 minutes at room temperature, and bioluminescence detected on a GloMax® luminometer. After reading, the duplicate wells were averaged, and the averaged values with peroxide addition were compared to those without peroxide (Table 11).

TABLE 11

| | | Averaged Relative Light Unit Values | | | | | |
|---|---|---|---|---|---|---|---|
| | | RT plate | | | 37 C. plate | | |
| Media | Compound | 0 uM Per | 5 uM Per | 10 uM Per | 0 uM Per | 5 uM Per | 10 uM Per |
| HBSS | PBI 4458 | 853,268 | 6,111,214 | 10,641,411 | 434,728 | 2,791,805 | 4,912,905 |
| HBSS | PBI 4472 | 103,738 | 1,106,195 | 2,058,421 | 44,007 | 424,851 | 715,803 |
| DMEM | PBI 4458 | 2,075,191 | 8,556,256 | 16,016,143 | 986,772 | 5,686,033 | 12,130,782 |
| DMEM | PBI 4472 | 921,496 | 4,304,645 | 8,071,553 | 400,077 | 3,083,589 | 5,340,569 |

As seen in Table 11, the "0 µM peroxide" values at 37° C. were lower than at RT, and signals from reactions in DMEM were greater than in HBSS, suggesting that some component in DMEM (either on not present or at a different concentration in HBSS) affects the signal strength. While the exact cause of the signal differences seen between reactions performed at room temperature vs. 37° C. is not known, the background reduction seen upon incubating these two compounds in DMEM at 37° C. suggests they will work well as hydrogen peroxide sensors with mammalian cells grown in DMEM. The strong signal from PBI 4458 in media compared to PBI 3048 or 4480 in B may be the result of this background reduction. Additional examples for 9547 US00

Example 18

Detection of Reactive Oxygen Generation Using Coelenterazine Borates

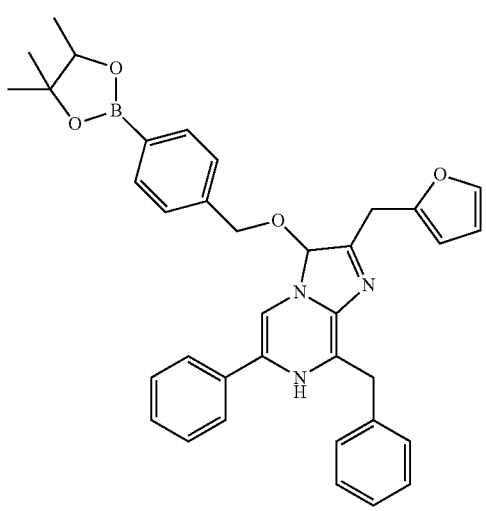

PBI 4759

PBI 4759 (10 mM; final concentration 12.5 uM), various concentrations of hydrogen peroxide and 40 ng/ml NanoLuc™ luciferase enzyme (Promega Corporation) were added to wells of a 96-well assay plate containing 200 mM Tris-Cl either at pH 8.5 or pH 9.0. Luminescence was detected on a GloMax® luminometer.

The results indicate the PBI 4759 allows sensitive detection of hydrogen peroxide (FIG. 3). The signal is proportional to the level of hydrogen peroxide (H2O2) present in the reaction and is also dependent upon the presence of NanoLuc™ luciferase enzyme (NL). Note that although the first boxed set of numbers in FIG. 3 are labeled with columns with "NL with H2O2" and "No NL with H2O2"; in fact these reactions did not contain any $H_2O_2$ and acted as a control for the other additions.

Example 19

Background Reduction of PBI 4472

PBI 4472 (50 µM) was incubated with assay buffer (100 mM Tris base, pH 10.4) for 15 minutes at room temperature. The samples were then either treated with a background reduction reagent (BRR; TCEP) or remained untreated. After a 15 minute incubation at room temperature, luciferin detection reagent with 1 mM D-cysteine (Promega Corporation) was added to the samples and incubated for 20 minutes at room temperature. Luminescence was detected on a Tecan F500 plate reader.

The results demonstrate that the addition of a reduction reagent can reduce background that may be seen with the luciferin borates such as PBI 4472 (FIG. 4).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

16. A compound of formula
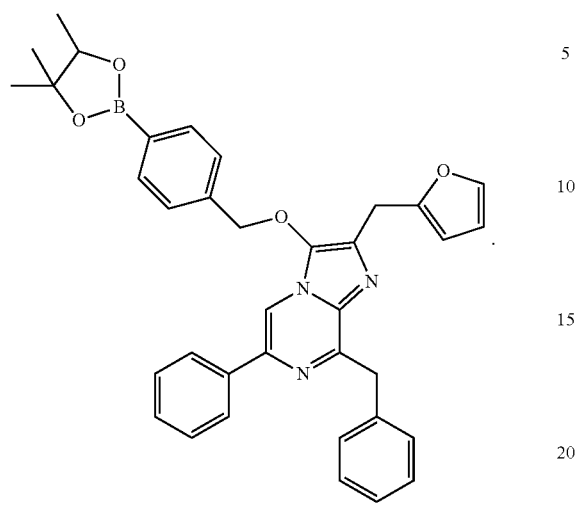

The invention claimed is:

1. A compound according to Formula (II):

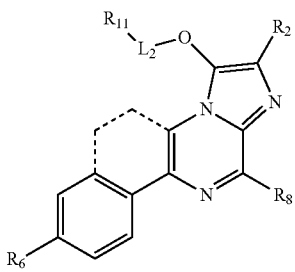

wherein $R_{11}$ is boronic acid or a borate ester;

$R^2$ is —$(CH_2)_n$-T or $C_{1-5}$ alkyl;

$R^6$ is selected from the group consisting of —H, —OH, —$NH_2$—OC(O)R or —$OCH_2OC(O)R$;

$R^8$ is selected from the group consisting of

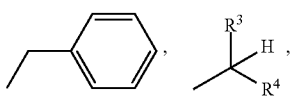

H or lower cycloalkyl;
wherein $R^3$ and $R^4$ are both H or both $C_{1-2}$ alkyl;
n is 0 to 3;
each R is independently a $C_{1-2}$ alkyl;
T is aryl, heteroaryl, substituted aryl, substituted heteroaryl or cycloalkyl;
$L_2$ is a linker;
and the dashed bonds indicate the presence of an optional ring which may be saturated or unsaturated.

2. A compound according to claim 1, wherein $L_2$ is

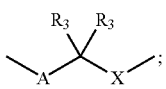

A is $-C_6(R_{10})_4-$ or $-(CR_{21}-CR_{21})_n-$ or $-O-C_6(R_{10})_4-$ or $-S-C_6(R_{10})_4-$ or $-NR'-C_6(R_{10})_4-$ or a direct bond; R' is H or $C_{1-4}$ alkyl; each $R_3$ is independently halo, H, $C_{1-4}$ alkyl, $C_{1-4}$ hydroxyalkyl, or $C_{1-4}$ alkylcarboxylic acid; each $R_{10}$ is independently H, halo, $CH_3$, $OCH_3$, or $NO_2$; each $R_{21}$ is independently H or $CH_3$; n is 1 or 2; and X is selected from a direct bond, $-C(O)-$, and $-C(O)NR_{22}$, where $R_{22}$ is H or $C_{1-4}$ alkyl.

3. A compound according to claim 1, wherein $R_{11}$ is

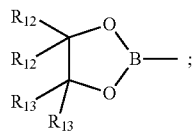

and
each $R_{12}$ and $R_{13}$ is independently selected from H, $C_{1-4}$ alkyl, $CF_3$, phenyl or substituted phenyl; or $R_{12}$ and $R_{13}$ together can be an alkyl ring having from 3-7 carbons or can be replaced by a fused 6-membered aromatic ring.

4. A compound according to claim 1, wherein $R_{11}$ is

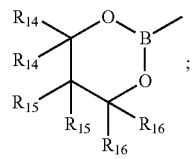

and
each $R_{14}$, $R_{15}$ and $R_{16}$ is independently selected from H, $C_{1-4}$ alkyl, $CF_3$, phenyl and substituted phenyl; or both $R_{15}$ together can form an alkyl ring having from 3-7 carbons; $R_{14}$ and $R_{15}$ together or $R_{15}$ and $R_{16}$ together can be an alkyl ring having from 3-7 carbon atoms or can be replaced by a 6-membered aromatic ring.

5. A compound according to claim 1, wherein:
$R^2$ is

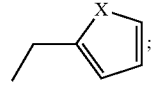

and X is O or S.

6. A compound according to claim 1, wherein $R^2$ is $C_{2-5}$ straight-chain alkyl.

7. A compound according to claim 1, wherein $R^8$ is

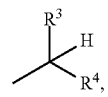

lower cycloalkyl or H, wherein $R^3$ and $R^4$ are both H or $C_{1-2}$ alkyl.

8. A compound according to claim 1, wherein, $R^8$ is benzyl.

9. A method of detecting hydrogen peroxide in a cell comprising:
    (a) contacting cells with a compound according to claim 1;
    (b) adding a luciferase reaction mixture to the contacted cells; and
    (c) measuring bioluminescence thereby detecting the presence of hydrogen peroxide in the cell.

10. The method of claim 9, wherein the cell is in an animal or in a sample.

11. A method of detecting hydrogen peroxide in a cell comprising:
    (a) contacting cells with a compound according to claim 1 in a first reaction vessel to form an incubation mixture;
    (b) transferring at least a portion of the incubation mixture to a second reaction vessel;
    (c) adding a luciferase reaction mixture to the second reaction vessel; and
    (d) measuring bioluminescence thereby detecting the presence of hydrogen peroxide in the cell.

12. The method of claim 11, wherein the cell is in an animal or in a sample.

13. A method of determining the effect of a test compound or test condition on the presence or amount of hydrogen peroxide in a sample comprising:
    a) treating a sample with a test compound or test condition,
    b) contacting the sample from a) with a compound according to claim 1;
    c) adding a luciferase reaction mixture to the sample;
    d) measuring bioluminescence.

14. The method of claim 13, wherein the sample comprises a cell, cell medium or physiological sample from an animal.

15. A kit comprising a compound according to claim 1.